United States Patent
Denis et al.

(10) Patent No.: US 9,737,505 B2
(45) Date of Patent: *Aug. 22, 2017

(54) PRODRUG OF 1,1'-(1,6-DIOXO-1,6-HEXANEDIYL)BIS-D-PROLINE

(71) Applicant: GlaxoSmithKline Intellectual Property Development Limited, Brentford, Middlesex (GB)

(72) Inventors: Alexis Denis, Les Ulis (FR); Olivier Mirguet, Les Ulis (FR); Jérôme Toum, Les Ulis (FR)

(73) Assignee: GlaxoSmithKline Intellectual Property Development Limited, Brentford, Middlesex (GB)

(*) Notice: Subject to any disclaimer, the term of this patent is extended or adjusted under 35 U.S.C. 154(b) by 0 days.

This patent is subject to a terminal disclaimer.

(21) Appl. No.: 14/925,350

(22) Filed: Oct. 28, 2015

(65) Prior Publication Data

US 2016/0081983 A1    Mar. 24, 2016

Related U.S. Application Data

(63) Continuation-in-part of application No. 14/787,608, filed as application No. PCT/EP2015/058998 on Apr. 27, 2015.

(30) Foreign Application Priority Data

Apr. 29, 2014    (GB) .................................. 1407506.3

(51) Int. Cl.
| | |
|---|---|
| *A61K 31/4025* | (2006.01) |
| *A61K 39/395* | (2006.01) |
| *C07D 405/14* | (2006.01) |
| *A61K 45/06* | (2006.01) |

(52) U.S. Cl.
CPC ...... *A61K 31/4025* (2013.01); *A61K 39/3955* (2013.01); *A61K 45/06* (2013.01); *C07D 405/14* (2013.01)

(58) Field of Classification Search
None
See application file for complete search history.

(56) References Cited

U.S. PATENT DOCUMENTS

2011/0166329 A1* 7/2011 Pepys .................. A61K 31/401
530/387.3
2016/0075694 A1    3/2016 Denis et al.

FOREIGN PATENT DOCUMENTS

| EP | 1870412 A1 | 12/2007 |
|---|---|---|
| WO | WO 03/051836 A1 | 6/2003 |
| WO | WO 2004/108131 A1 | 12/2004 |
| WO | WO 2004/108733 A1 | 12/2004 |
| WO | WO2011107480 * | 9/2011 |

OTHER PUBLICATIONS

Wikipedia 2016 "Amyloidosis" accessed from wikipedia.org on Jun. 3, 2016 (excerpt only).*
Aesop Cho. Annual Reports in Medicinal Chemistry, 41: 395-407 (2006).
Norris, et al. Organic Process Research & Development, 9: 432-439 (2005).
Tennent, et al. Proc. Natl. Acad. Sci. USA 92: 4299-4303 (1995).
Non-Final Office Action, U.S. Appl. No. 14/787,608, dated Jan. 13, 2017.

* cited by examiner

*Primary Examiner* — Adam M Weidner
(74) *Attorney, Agent, or Firm* — Duke M. Fitch; Kathryn A. Lutomski; Edward R. Gimmi

(57) ABSTRACT

The compound (2R,2'R)-bis(((((tetrahydro-2H-pyran-4-yl) oxy)carbonyl)oxy)methyl) 1,1'-adipoylbis(pyrrolidine-2-carboxylate) possesses physicochemical properties suitable for pharmaceutical development and is capable of generating (R)-1-[6-[(R)-2-carboxy-pyrrolidin-1-yl]-6-oxo-hexanoyl]pyrrolidine-2-carboxylic acid (CPHPC) in quantities capable of depleting serum amyloid P component (SAP) efficiently following oral administration, making it useful in the treatment of amyloidosis, Alzheimer's disease, type 2 diabetes mellitus and osteoarthritis.

16 Claims, 5 Drawing Sheets

US 9,737,505 B2

PRODRUG OF 1,1'-(1,6-DIOXO-1,6-HEXANEDIYL)BIS-D-PROLINE

FIELD OF THE INVENTION

The present invention relates to the novel compound (2R,2'R)-Bis(((((tetrahydro-2H-pyran-4-yl)oxy)carbonyl)oxy)methyl) 1,1'-adipoylbis(pyrrolidine-2-carboxylate), pharmaceutical compositions comprising the same and the use of the same for treatment of diseases or disorders wherein depletion of serum amyloid P component (SAP) would be beneficial.

BACKGROUND TO THE INVENTION

Serum amyloid P component (SAP) is a normal, structurally invariant, soluble, non-fibrillar, constitutive plasma glycoprotein, mass 127,310 Da, produced exclusively by the liver. It is composed of 5 identical 25,462 Da protomers non-covalently associated with cyclic pentameric symmetry in a disc like configuration. Each subunit, composed of a flattened β-jellyroll, with tightly tethered loops joining the β-strands, contains a single calcium dependent ligand binding site on the planar B (binding) face of the intact pentamer. SAP binds to all types of amyloid fibrils with the high avidity conferred by multivalent interactions. This strictly calcium dependent interaction is responsible for the universal presence of human SAP in all human amyloid deposits of all types, and hence the name of the protein, where P stands for plasma, the source of this component of amyloid. In addition to its capacity for specific calcium dependent binding to particular ligands, a key property of human SAP is that the protein itself is intrinsically resistant to proteolysis. Its avid binding to amyloid fibrils is mutually stabilising, strongly protecting the fibrils against proteolysis and phagocytic degradation in vitro[1] and significantly contributing to persistence of amyloid in vivo[2]. These observations underlie the validation of SAP as a therapeutic target in amyloidosis (M B Pepys & T L Blundell, U.S. Pat. No. 6,126,918, 3 Oct. 2000). Furthermore, binding of SAP to nascent amyloid fibrils strongly promotes amyloid fibrillogenesis[3-5]. European patent application EP 0915088 discloses compounds which are competitive inhibitors of binding of SAP to amyloid fibrils, as well as methods for their manufacture. One of the compounds disclosed therein is (R)-1-[6-[(R)-2-carboxy-pyrrolidin-1-yl]-6-oxo-hexanoyl]pyrrolidine-2-carboxylic acid (CPHPC).

Administration of these palindromic bivalent ligands for SAP causes the rapid and almost complete depletion of SAP from the circulation for as long as the compounds are administered[6,7], as described in WO2003/013508, U.S. Pat. No. 7,045,499; U.S. Pat. No. 7,691,897; and U.S. Pat. No. 8,173,694. This treatment also reduces the amount of SAP associated with the amyloid deposits but does not remove all the SAP[7].

Amyloid is an abnormal, insoluble, extracellular deposit, composed predominantly of characteristic protein fibrils[8] together with abundant proteoglycans and glycosaminoglycans. About 25 different, unrelated, natively soluble, globular proteins form the amyloid fibrils which cause the different types of systemic amyloidosis but all amyloid fibrils have very similar morphology and the same cross-β core structure. This structure binds the ordered arrays of Congo red dye molecules which create pathognomonic red-green birefringence in strong cross polarised light: the gold standard diagnostic criterion for amyloid. Certain soluble, non-fibrillar plasma proteins may also be present in amyloid deposits but only one, serum amyloid P component (SAP), is universal in all human amyloid deposits, due to its avid, specific, calcium dependent binding to all types of amyloid fibrils.

Amyloid deposits disrupt the structure and function of affected tissues and organs, causing the serious disease, amyloidosis. Systemic amyloidosis is a rare, fatal condition caused by amyloid deposits which may be present in connective tissue and blood vessel walls throughout the body, as well as the parenchyma of the major organs, but never in brain substance itself. In local amyloidosis, the amyloid deposits are confined to a single anatomical site or a single organ/tissue system. Cerebral amyloid angiopathy, with amyloid deposition confined to the walls of cerebral blood vessels, is the most common and important form of local amyloidosis. It is responsible for a substantial proportion of intracerebral haemorrhages in both demented Alzheimer's disease patients and non-demented individuals, and is thus an important cause of dementia in its own right.

Treatment of systemic amyloidosis patients with CPHPC produced almost complete depletion of circulating SAP for as long as the drug was administered but did not remove all the SAP bound to the amyloid deposits.[7] The patients remained clinically stable while being treated, with no new amyloid accumulation, and their organ function was maintained but there was no regression of amyloid, probably due to the failure of complete removal of amyloid bound SAP. Since the amyloid deposits in the tissues are the direct cause of disease, it is highly desirable that they should be eliminated. This important unmet medical need led to the invention of a new approach to treatment of amyloidosis in which SAP bound to amyloid deposits is used as a target for anti-human SAP antibodies. Such antibodies could not be safely or effectively administered to patients with normal circulating concentrations of SAP since the antibodies would bind to the SAP in the plasma, forming tissue damaging immune complexes, and the antibodies would be consumed in this process making them unavailable for binding to SAP in amyloid. However prior administration of CPHPC depletes SAP from the circulation, so that anti-SAP antibodies can be safely infused and remain available to bind to residual SAP left in the amyloid deposits. Binding of the antibodies to the amyloid-associated SAP activates the complement system and engages macrophages to phagocytose and destroy the amyloid deposits leading to clinical benefit.

International patent application WO2009/000926 discloses the use of compounds which deplete SAP from the circulation co-administered with an antibody specific for SAP for potential treatment of amyloidosis.

International patent application WO2009/155962 discloses mouse monoclonal antibody Abp1 and provides binding and efficacy data for various mouse monoclonal antibodies which may be co-administered with compounds which deplete SAP from the circulation for potential use in the treatment of amyloidosis.

International patent application WO2011/107480 discloses antigen binding proteins, in particular humanised antibodies, specific for SAP and their potential use in the treatment of diseases associated with amyloid deposition.

In addition to the rare clinical condition of amyloidosis, which is unequivocally directly caused by extracellular amyloid deposition disrupting tissue structure and function, amyloid deposits are also present in two very common and important diseases: Alzheimer's disease and type 2 diabetes. In these latter diseases, the amyloid deposits are microscopic, are confined to the brain and islets of Langerhans respectively, and it is not known whether or how they may contribute to pathogenesis of neurodegeneration and diabetes respectively. Alzheimer's disease and type 2 diabetes thus cannot be classified as forms of amyloidosis but rather should be considered as amyloid associated diseases. Nevertheless, amyloid deposits are always present in them and the deposits also always contain SAP[15-19]. The brain in Alzheimer's disease also contains another type of abnormal insoluble fibrillar protein aggregate, known as neurofibrillary tangles, and SAP binds avidly to these, as it does to amyloid.[15-19] Neurofibrillary tangles bearing SAP, but not amyloid, are present in the brain in other types of dementia, including the frontotemporal dementias In addition to, and quite independent of, its role in amyloidosis, human SAP binds to and enters cerebral neurones and causes neuronal apoptosis in vitro and in vivo[9-13]. It has been shown that unique, pharmaceutical grade pure human SAP[14] disrupts synaptic transmission, causing abnormal paired pulse ratio and long term potentiation in organotypic rodent brain slices in vitro.

The cerebral neurotoxicity of human SAP is therefore likely to contribute to neurodegeneration in humans[9-12,20]. The fact that most of the common risk factors for dementia increase brain exposure to SAP is consistent with this concept. Thus age, a key risk factor, is associated with prolonged exposure of the ageing brain to normal SAP concentrations, whilst the major risk factors of non-penetrating head trauma and cerebral haemorrhage cause blood to enter the brain, sharply increasing cerebral SAP content. In Alzheimer's disease, brain content of SAP is abnormally high due to its binding to amyloid deposits and neurofibrillary tangles[15-19]. This is also likely to be the case in other dementias with neurofibrillary tangles but not amyloid deposits. Importantly, higher brain SAP content is reported in demented Alzheimer's disease patients than in elderly subjects who were cognitively intact at death, either with or without co-existing plaques and tangles at autopsy[20]. The significant positive correlation between cerebral SAP content and dementia[20] is consistent with a causative role for SAP.

The quantities of SAP in cerebrospinal fluid and bound to cerebral amyloid deposits and neurofibrillary tangles are dramatically lower than in systemic extracellular fluid and on systemic amyloid deposits respectively. Depletion of plasma SAP by CPHPC, from the normal 20-50 mg/L to <0.1 mg/L, reduces the CSF SAP concentration from 2-30 µg/L to <0.1 µg/L in patients with Alzheimer's disease[21]. Human SAP is produced only by the liver and reaches the brain via the blood[22]. CPHPC treatment thus removes virtually all SAP from the cerebrospinal fluid and, since SAP binding is fully reversible, will also remove it from the cerebral amyloid deposits and neurofibrillary tangles. Furthermore in Alzheimer's disease patients, CPHPC enters the cerebrospinal fluid[21] where it can also block binding of any free SAP to amyloid fibrils, to neurofibrillary tangles and cerebral neurones. All amyloid fibril types can be degraded by proteases and phagocytic cells in vitro[1], and systemic amyloid deposits spontaneously regress slowly in vivo when the abundance of their respective fibril precursor proteins is sufficiently reduced[8]. Mechanisms for amyloid clearance thus do operate in vivo. Confirmation that human SAP is itself neurocytotoxic[9-13], independent of its binding to amyloid, demonstrates the potential, additional, direct benefit of SAP depletion.

All plasma proteins enter diseased or damaged joints in vivo but in patients with various different arthropathies, uptake of radiolabelled SAP into some joints that did not have clinically detectable effusions was observed. Furthermore the concentration of SAP in synovial effusion fluids was substantially below that predicted from the molecular size of SAP, demonstrating that the SAP visualised scintigraphically was not free in solution but was actually bound to solid structures within the joint. Synovium, articular cartilage and/or joint capsules of elderly individuals often contain microscopic amyloid deposits, associated with age rather than extent or severity of osteoarthritis, and these deposits could explain the localisation of SAP. SAP also binds avidly, in vivo as well as in vitro, to exposed DNA and chromatin, and to apoptotic cells. Increased cell death in osteoarthritic joints may thus provide ligands for SAP deposition. WO2004/108131 discloses the treatment of patients with osteoarthritis by injection of CPHPC ((R)-1-[6-[(R)-2-carboxy-pyrrolidin-1-yl]-6-oxo-hexanoyl]pyrrolidine-2-carboxylic acid) resulting in the alleviation of osteoarthritis symptoms.

Human SAP binds avidly to all forms of free DNA and also to chromatin, both in vitro and in vivo. Indeed SAP is the only normal human plasma protein which binds specifically in a calcium dependent interaction with DNA[23,24]. In contrast, SAP from some other species, including mouse and horse, binds weakly if at all to DNA, and dogs and rabbits do not even have the SAP gene and thus produce no SAP. DNA vaccination, in which immunisation is achieved by injection of DNA coding for the immunogen rather by injection of the immunogen itself, has been extensively investigated as a highly desirable approach to induction of protective immunity against infections and as a potential immunotherapeutic intervention in cancer. However, although DNA vaccination is effective in mice. dogs, rabbits and horses, it has consistently failed in humans and also in cows, which like humans have SAP which binds avidly to DNA. In the species in which DNA vaccination works, SAP either does not bind to DNA or is absent. Furthermore, experiments in mice with transgenic expression of human SAP and using CPHPC to deplete it, confirm that the presence of human SAP blocks efficacy of DNA vaccination.[25,26]

SAP binds to some bacterial species but not to others. For those pathogenic bacteria to which SAP binds, the SAP has a powerful anti-opsonic effect in vitro and in vivo, reducing phagocytosis and killing of the organisms and thus protecting them from the host's innate immune system[27]. This effect, which promotes infectivity and virulence, is abrogated by administration of CPHPC to inhibit binding of SAP to the bacteria[27]. SAP is also present bound to the surface of the fungal cells in the tissues of patients suffering from invasive candidiasis[28]. This binding reflects the presence of amyloid fibrils, formed from fungal proteins, on the surface of the pathogenic organism.[28]

CPHPC is pharmacologically effective but it has very low and variable oral bioavailability of ~3-5% and therefore only parenteral administration by intravenous infusion or subcutaneous injection is optimal to achieve the desired SAP depletion. However most of the existing and potential indications for therapeutic SAP depletion require long term administration. Long term intravenous administration is not practical. Although long term subcutaneous administration is feasible, the injections may cause stinging discomfort and this is not tolerated by some patients.[7]

WO2003/051836 discloses D-prolines pro-drugs useful for the treatment of diseases where SAP depletion has a beneficial effect. The 25 Examples disclosed therein were predominantly obtained as oils; only 5 of them were solid. In proceedings at the European Patent Office, a divisional application to the European equivalent of WO2003/051836 was filed with claims directed to (R)-1-(6-{(R)-2-[1-(2,2-dimethyl-propionyloxy)-ethoxycarbonyl]-pyrrolidin-1-yl}-6-oxo-hexanoyl)-pyrrolidine-2-carboxylic acid 1-(2,2-dimethyl-propionyloxy)-ethyl ester. At the time of filing, the GlaxoSmithKline group of companies (Glaxo Group Limited) has a Licence and Research Collaboration Agreement with Pentraxin Therapeutics Limited including a licence to EP 0915088 and WO2003/051836, and corresponding applications thereof.

There is therefore a need for a compound which is capable of generating CPHPC in quantities capable of depleting SAP efficiently following oral administration, whilst possessing physicochemical properties suitable for pharmaceutical development.

SUMMARY OF THE INVENTION

It has surprisingly been found that the compound (2R, 2'R)-bis(((((tetrahydro-2H-pyran-4-yl)oxy)carbonyl)oxy)methyl) 1,1'-adipoylbis(pyrrolidine-2-carboxylate) according to Formula (I) possesses physicochemical properties suitable for pharmaceutical development and is capable of generating CPHPC in quantities capable of depleting SAP efficiently following oral administration.

Accordingly, in a first aspect, the present invention provides a compound (2R,2'R)-bis(((((tetrahydro-2H-pyran-4-yl)oxy)carbonyl)oxy)methyl) 1,1'-adipoylbis(pyrrolidine-2-carboxylate) according to Formula (I):

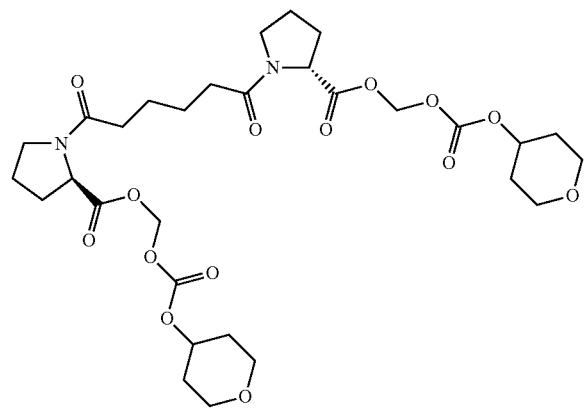 [SMILES: O=C(OCOC(=O)[C@H]1CCCN1C(=O)CCCCC(=O)N1CCC[C@@H]1C(=O)OCOC(=O)OC1CCOCC1)OC1CCOCC1]

(I)

The compound of Formula (I) is referred to hereinafter as "the compound of the invention".

The compound of the invention exhibits good physiochemical properties and is capable of generating CPHPC in quantities capable of depleting SAP efficiently following oral administration.

The compound of Formula (I) has good pH solution stability and intestinal microsome stability, and low liver microsome stability, readily generating CPHPC, suggesting the compound of Formula (I) will readily generate circulating levels of CPHPC on oral dosing in humans. Also, it does not show any interaction with cytochrome p450, suggesting the compound of Formula (I) will not show CYP450 mediated drug-drug interactions (DDIs). Additionally, the compound of Formula (I) is highly crystalline, which is advantageous with respect to formulation of the active substance and manufacture of the pharmaceutical product.

The use of a compound with this profile may result in advantages in the treatment of diseases or disorders wherein depletion of SAP (serum amyloid P component) would be beneficial, for example in amyloidosis (including systemic amyloidosis and local amyloidosis), Alzheimer's disease, type II diabetes, osteoarthritis, bacterial infection, invasive candiasis and other fungal infections, and in conjunction with administration of DNA vaccines.

In a further aspect the invention provides a pharmaceutical composition, which comprises a therapeutically effective amount of a compound of Formula (I) and optionally one or more pharmaceutically acceptable carriers and/or excipients.

In a further aspect there is provided a compound of Formula (I) or one or more pharmaceutical compositions herein described for the depletion of circulating SAP in a subject.

In a further aspect there is provided the compound of Formula (I) or one or more pharmaceutical compositions herein described, for use in the treatment of diseases wherein SAP depletion would be beneficial.

In a further aspect there is provided a method of treatment of a disease or disorder wherein SAP depletion would be beneficial.

In a further aspect there is provided the use of a compound of Formula (I) or one or more pharmaceutical compositions herein described, in the manufacture of a medicament for use in the treatment of diseases wherein SAP depletion would be beneficial.

In a further aspect there is provided a kit of parts comprising one or more dosage forms of an anti-SAP antibody (in particular an antibody as disclosed in WO2011/107480) and one or more dosage forms of the compound of Formula (I).

DETAILED DESCRIPTION OF THE INVENTION

Definitions

Figure 1:
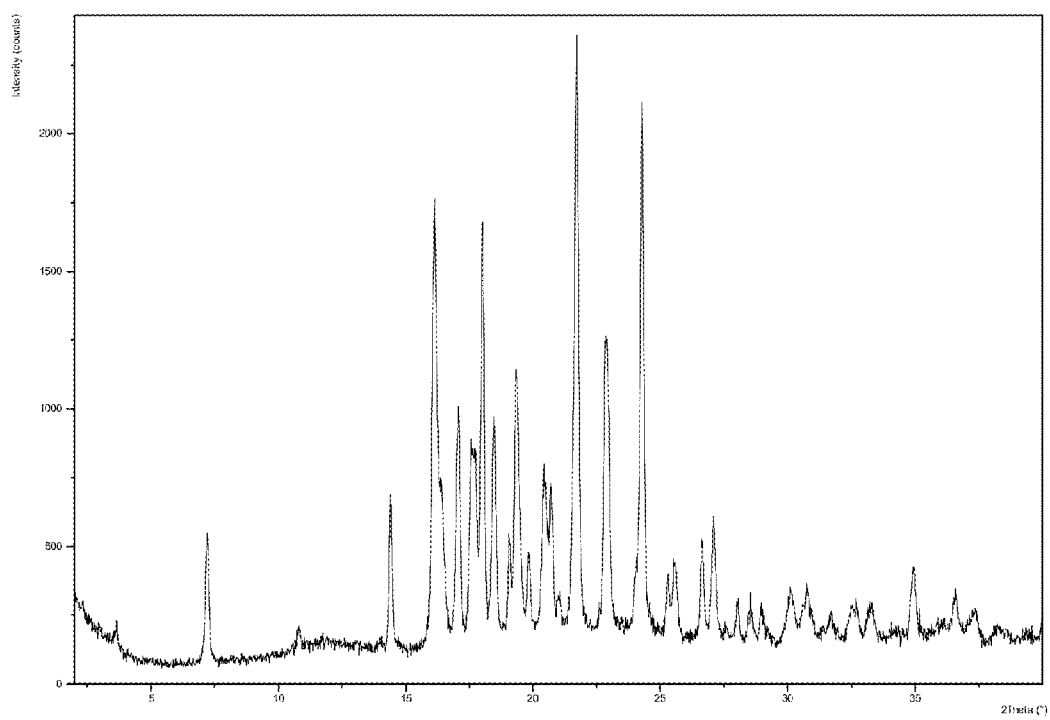
FIG. 1 shows an X-ray powder diffraction pattern (XRPD) of the crystalline solid form of the compound of Formula (I).

The following terms are intended to have the meanings presented herewith below and are useful in understanding the description and the scope of the present invention.

"Pharmaceutically acceptable" means approved or approvable by a regulatory agency of the Federal government of the United States of America or the corresponding agency in countries other than the United States of America (such as the EMA, the European Medicines Agency), or that is listed in the United States Pharmacopeia or European Pharmacopoeia (Ph. Eur.).

"Therapeutically effective amount" means the amount of a compound that, when administered to a subject for treating a disease, is sufficient to effect such treatment for the disease.

The term "antibody" is used in the broadest sense to refer to molecules with an immunoglobulin-like domain and includes monoclonal, recombinant, polyclonal, chimeric, humanised, human, bispecific and heteroconjugate antibodies; and antigen binding fragments. An antibody according to the present invention activates the human complement system and/or results in regression of amyloid deposits.

It will be appreciated that reference to "treatment" includes acute treatment or prophylaxis as well as the alleviation of established symptoms and/or retardation of progression of the disease, and may include the suppression of symptom recurrence in an asymptomatic patient.

The term "anti-SAP" in relation to an "antibody", i.e. an "anti-SAP antibody", means an antibody that binds to human SAP with no or insignificant binding to any other proteins, including closely related molecules such as C-reactive protein (CRP).

The term "CDR" means complementarity determining region. A CDR of an antibody as used herein means a CDR as determined using any of the well known CDR numbering methods, including Kabat, Chothia, AbM and contact methods.

By "circulating SAP" is meant SAP that is present in free form in the plasma in vivo and in vitro and is not associated with amyloid deposits in the tissues.

Pharmaceutical Compositions

In order to use the compound of Formula (I) in therapy, it will normally be formulated into a pharmaceutical composition in accordance with standard pharmaceutical practice.

The invention therefore provides a pharmaceutical composition, which comprises a therapeutically effective amount of a compound of Formula (I) and optionally one or more pharmaceutically acceptable carriers and/or excipients.

The present invention also provides a process for preparing a pharmaceutical composition, the process comprising admixing a therapeutically effective amount of a compound of Formula (I) and optionally one or more pharmaceutically acceptable carriers and/or excipients.

The present invention also provides a dosage form comprising the pharmaceutical composition of the invention.

A pharmaceutical composition of the invention, which may be prepared by admixture, suitably at ambient temperature and atmospheric pressure, is usually adapted for oral administration and, as such, may be in the form of tablets, capsules, oral liquid preparations, powders, granules, or lozenges.

In one embodiment, there is provided the pharmaceutical composition of the invention for oral administration.

Tablets and capsules for oral administration may be in unit dose form, and may contain conventional excipients, such as binding agents (e.g. pregelatinised maize starch, polyvinylpyrrolidone or hydroxypropyl methylcellulose); fillers (e.g. lactose, microcrystalline cellulose or calcium hydrogen phosphate); tabletting lubricants (e.g. magnesium stearate, talc or silica); disintegrants (e.g. potato starch or sodium starch glycollate); and acceptable wetting agents (e.g. sodium lauryl sulphate). The tablets may be coated according to methods well known in normal pharmaceutical practice.

Oral liquid preparations may be in the form of, for example, oily suspension, non-aqueous solutions, emulsions, syrups or elixirs, or may be in the form of a dry product for reconstitution with suitable aqueous or non-aqueous vehicle immediately prior to administration. Such liquid preparations may contain conventional additives such as suspending agents (e.g. sorbitol syrup, cellulose derivatives or hydrogenated edible fats), emulsifying agents (e.g. lecithin or acacia), non-aqueous vehicles (which may include edible oils e.g. almond oil, oily esters, ethyl alcohol or fractionated vegetable oils), preservatives (e.g. methyl or propyl-p-hydroxybenzoates or sorbic acid), and, if desired, conventional flavourings or colorants, buffer salts and sweetening agents as appropriate. Preparations for oral administration may be suitably formulated to give controlled release of the active compound.

In another embodiment, the dosage form is a tablet or a capsule.

The composition may contain from 0.1% to 99% by weight, preferably from 10 to 60% by weight, of the active material, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 5000 mg, 1.0 to 1000 mg, or 100 to 600 mg, for example 100, 200 or 300 mg, and such unit doses may be administered more than once a day, for example two or three times a day. Such therapy may extend for a number of days, weeks, months or years.

The invention further provides the compound of Formula (I) or a pharmaceutical composition as herein described, as for use in therapy.

The compound of Formula (I) is therefore of use in the treatment of diseases wherein SAP depletion would be beneficial.

The invention further provides the compound of Formula (I) or a pharmaceutical composition as herein described, for use in depletion of SAP.

In a further aspect there is provided a method of treatment of a disease or disorder in a subject wherein SAP depletion would be beneficial, which method comprises administration of a therapeutically effective amount of the compound of Formula (I).

In a further aspect there is provided a method of treatment of a disease or disorder in a subject wherein SAP depletion would be beneficial, which method comprises administration of a therapeutically effective amount of a pharmaceutical composition as herein described.

The invention further provides a method of depletion of SAP in a subject, which method comprises administering to the subject a therapeutically effective amount of the compound of Formula (I).

The invention further provides a method of depletion of SAP in a subject, which method comprises administering to the subject a therapeutically effective amount of a pharmaceutical composition as herein described.

Many forms of transmissible spongiform encephalopathy (prion diseases) are associated with amyloid deposits in the brain, and the present invention therefore relates to all these diseases or disorders, including variant Creutzfeldt-Jakob disease in humans, Creutzfeldt-Jakob disease itself, kuru and the various other forms of human prion disease, and also bovine spongiform encephalopathy, chronic wasting disease of mule-deer and elk, and transmissible encephalopathy of mink.

The invention further provides a method of treatment of a disease or disorder in a subject, wherein the disease or disorder is selected from the group consisting of amyloidosis, Alzheimer's disease, type 2 diabetes mellitus, osteoarthritis, bacterial infections, invasive candiasis, transmissible spongiform encephalopathy, variant Creutzfeld-Jakob disease in humans, Creutzfeld-Jakob disease, kuru, other human prion diseases, bovine spongiform encephalopathy, chronic wasting disease of mule-deer and elk, and transmissible encephalopathy of mink, which method comprises administering to the subject a therapeutically effective amount of the compound of Formula (I).

The invention further provides a method of treatment of a disease or disorder in a subject, wherein the disease or disorder is selected from the group consisting of amyloidosis, Alzheimer's disease, type 2 diabetes mellitus, osteoarthritis, bacterial infections, invasive candiasis, transmissible spongiform encephalopathy, variant Creutzfeld-Jakob disease in humans, Creutzfeld-Jakob disease, kuru, other human prion diseases, bovine spongiform encephalopathy, chronic wasting disease of mule-deer and elk, and transmissible encephalopathy of mink, which method comprises administering to the subject a therapeutically effective amount of a pharmaceutical composition as herein described.

The invention further provides a method of treatment of a disease or disorder in a subject, wherein the disease or disorder is selected from the group consisting of amyloidosis, Alzheimer's disease, type 2 diabetes mellitus and osteoarthritis, which method comprises administering to the subject a therapeutically effective amount of the compound of Formula (I).

The invention further provides a method of treatment of a disease or disorder in a subject, wherein the disease or disorder is selected from the group consisting of amyloidosis, Alzheimer's disease, type 2 diabetes mellitus and osteoarthritis, which method comprises administering to the subject a therapeutically effective amount of a pharmaceutical composition as herein described.

The invention further provides a method of treatment of a disease or disorder in a subject, wherein the disease or disorder is selected from the group consisting of Alzheimer's disease, type 2 diabetes mellitus and osteoarthritis, which method comprises administering to the subject a therapeutically effective amount of the compound of Formula (I).

The invention further provides a method of treatment of a disease or disorder in a subject, wherein the disease or disorder is selected from the group consisting of Alzheimer's disease, type 2 diabetes mellitus and osteoarthritis, which method comprises administering to the subject a therapeutically effective amount of a pharmaceutical composition as herein described.

The invention further provides a method of treatment of a disease or disorder in a subject, wherein the disease or disorder is amyloidosis, which method comprises administering to the subject a therapeutically effective amount of the compound of Formula (I).

The invention further provides a method of improvement of efficacy of human DNA vaccines, which method comprises administering to the subject a therapeutically effective amount of the compound of Formula (I).

The invention further provides a method of improvement of efficacy of human DNA vaccines, which method comprises administering to the subject a therapeutically effective amount of a pharmaceutical composition as herein described.

The invention further provides the use of the compound of formula (I) in combination with a DNA vaccine.

The invention further provides for the compound of Formula (I) for use in the improvement of the efficacy of human DNA vaccines.

The invention further provides for a pharmaceutical composition as herein described for use in the improvement of the efficacy of human DNA vaccines.

The invention further provides for the use of the compound of Formula (I) in the improvement of the efficacy of human DNA vaccines.

The invention further provides for the use of a pharmaceutical composition as herein described in the improvement of the efficacy of human DNA vaccines.

The invention further provides the use of the compound of Formula (I) in the manufacture of a medicament for use in the improvement of the efficacy of human DNA vaccines.

By "improvement in efficacy of human DNA vaccines" is meant enabling the DNA vaccine to induce immunoprotective immune responses against the immunogens encoded by the human DNA vaccine.

The subject may be a mammal. The subject is typically a human.

The invention further provides a method of treatment of a disease or disorder in a subject, wherein the disease or disorder is selected from the group consisting of transmissible spongiform encephalopathy, variant Creutzfeldt-Jakob disease in humans, Creutzfeldt-Jakob disease, kuru, bovine spongiform encephalopathy, chronic wasting disease of mule-deer and elk, and transmissible encephalopathy of mink, which method comprises administering to the subject a therapeutically effective amount of the compound of Formula (I).

The invention further provides a method of treatment of a disease or disorder in a subject, wherein the disease or disorder is selected from the group consisting transmissible spongiform encephalopathy, variant Creutzfeldt-Jakob disease in humans, Creutzfeldt-Jakob disease, kuru, bovine spongiform encephalopathy, chronic wasting disease of mule-deer and elk, and transmissible encephalopathy of mink, which method comprises administering to the subject a therapeutically effective amount of a pharmaceutical composition as herein described.

The term "amyloidosis" encompasses both systemic amyloidosis (including, but not limited to, AL-type amyloidosis, AA-type amyloidosis, dialysis amyloidosis, ATTR (transthyretin) amyloidosis, hereditary systemic amyloidosis) and local amyloidosis (including, but not limited to cerebral amyloid angiopathy).

In another aspect, the invention provides for the compound of Formula (I) or a pharmaceutical composition as herein described for use in the treatment of a disease or disorder wherein SAP depletion would be beneficial.

In another aspect, the invention provides for the compound of Formula (I) or a pharmaceutical composition as herein described for use in the depletion of SAP.

In one embodiment, the invention provides for the compound of Formula (I) or a pharmaceutical composition as herein described for use in the depletion of SAP in vivo.

In another aspect, the invention provides for the compound of Formula (I) for use in the treatment of a disease or disorder selected from the group consisting of amyloidosis, Alzheimer's disease, type 2 diabetes mellitus and osteoarthritis.

In another aspect, the invention provides for a pharmaceutical composition as herein described for use in the treatment of a disease or disorder selected from the group consisting of amyloidosis, Alzheimer's disease, type 2 diabetes mellitus and osteoarthritis.

In one embodiment, the invention provides for the compound of Formula (I) for use in the treatment of a disease or disorder selected from the group consisting of Alzheimer's disease, type 2 diabetes mellitus and osteoarthritis.

In one embodiment, the invention provides for the compound of Formula (I) for use in the treatment of amyloidosis.

In another aspect, the invention provides for a pharmaceutical composition as herein described for use in the treatment of a disease or disorder selected from the group consisting of Alzheimer's disease, type 2 diabetes mellitus and osteoarthritis.

In another aspect, the invention provides for a pharmaceutical composition as herein described for use in the treatment of amyloidosis.

In another aspect, the invention provides for the use of a compound of Formula (I) or one or more pharmaceutical compositions herein described in the treatment of a disease or disorder wherein SAP depletion would be beneficial.

In another aspect, the invention provides for the use of a compound of Formula (I) or one or more pharmaceutical compositions herein described in the depletion of SAP.

In another aspect, the invention provides for the use of a compound of Formula (I) in the treatment of a disease or disorder selected from the group consisting of amyloidosis, Alzheimer's disease, type 2 diabetes mellitus and osteoarthritis.

In another aspect, the invention provides for the use of a pharmaceutical composition herein described in the treatment of a disease or disorder selected from the group consisting of amyloidosis, Alzheimer's disease, type 2 diabetes mellitus and osteoarthritis.

In another aspect, the invention provides for the use of a compound of Formula (I) in the treatment of a disease or disorder selected from the group consisting of Alzheimer's disease, type 2 diabetes mellitus and osteoarthritis.

In another aspect, the invention provides for the use of a compound of Formula (I) in the treatment of amyloidosis.

In another aspect, the invention provides for the use of a pharmaceutical composition herein described in the treatment of a disease or disorder selected from the group consisting of Alzheimer's disease, type 2 diabetes mellitus and osteoarthritis.

In another aspect, the invention provides for the use of a pharmaceutical composition herein described in the treatment of amyloidosis.

In another aspect, the invention provides for the use of a compound of Formula (I) in the manufacture of a medicament for use in the treatment of a disease or disorder wherein SAP depletion would be beneficial.

In another aspect, the invention provides for the use of a compound of Formula (I) in the manufacture of a medicament for use in the depletion of SAP.

In another aspect, the invention provides for the use of a compound of Formula (I) in the manufacture of a medicament for use in the treatment of a disease or disorder selected from the group consisting of amyloidosis, Alzheimer's disease, type 2 diabetes mellitus and osteoarthritis.

In another aspect, the invention provides for the use of a compound of Formula (I) in the manufacture of a medicament for use in the treatment of a disease or disorder selected from the group consisting of Alzheimer's disease, type 2 diabetes mellitus and osteoarthritis.

In another aspect, the invention provides for the use of a compound of Formula (I) in the manufacture of a medicament for use in the treatment of amyloidosis.

When used for the treatment of amyloidosis, the compounds of Formula (I) may be administered with an anti-SAP antibody.

In an embodiment, the anti-SAP antibody binds to the A face of human SAP. In an embodiment, the anti-SAP antibody comprises the heavy chain complementarity determining regions (CDRs) present within SEQ ID NO:28 (SEQ ID NO:1) and the light chain CDRs present within SEQ ID NO:35 (SEQ ID NO:2) in WO 11/107480. In an embodiment the anti-SAP antibody comprises a heavy chain variable region of SEQ ID NO:28 (SEQ ID NO:1) and a light chain variable region of SEQ ID NO:35 (SEQ ID NO:2) in WO 11/107480. In an embodiment, the anti-SAP antibody comprises a human IgGl or IgG3 human constant domain. In an embodiment the anti-SAP antibody consists of a heavy chain of SEQ ID NO:62 (SEQ ID NO:3) and a light chain of SEQ ID NO:64 (SEQ ID NO:4) in WO 11/107480.

In an embodiment, the anti-SAP antibody comprises the heavy and light chain CDRs described within WO 11/107480 as SEQ ID NO:1 (SEQ ID NO:5), SEQ ID NO:2 (SEQ ID NO:6) and SEQ ID NO:3 (SEQ ID NO:7), SEQ ID NO:4 (SEQ ID NO:8), SEQ ID NO:5 (SEQ ID NO:9) and SEQ ID NO:6 (SEQ ID NO:10).

Therefore, in a further aspect, the invention provides for a method of treatment of amyloidosis which method comprises administering to a subject a therapeutically effective amount of a compound of Formula (I) or a pharmaceutical composition as herein described in co-administration with an anti-SAP antibody.

In one embodiment, the administration of the compound of Formula (I) in co-administration with an anti-SAP antibody is sequential.

Such sequential administration may be close in time (eg. simultaneously) or remote in time. Furthermore, it does not matter if the compounds are administered in the same dosage form, e.g. one compound may be administered intravenously and the other compound may be administered orally.

In a further embodiment, the compound of Formula (I) is administered first. In a further embodiment, the anti-SAP antibody is administered when the level of circulating SAP in the subject has been reduced to a level of less than 2 mg/L. In one embodiment, the level of circulating SAP has been reduced to a level of 1 mg/L or less. In a further embodiment the level of circulating SAP has been reduced to a level of 0.5 mg/L or less.

The level of circulating SAP can be measured using a commercially available ELISA (enzyme-linked immunosorbent assay) kit (e.g. HK331 Human SAP ELISA Kit from Hycult Biotech).

In a further embodiment, the compound of Formula (I) is administered for 5-8 days or until the level of the SAP circulating in the subject has been reduced to a level of less than 2 mg/L whichever is longer. In one embodiment, the level of the SAP circulating in the subject has been reduced to 1 mg/L or less. In a further embodiment, the level of SAP circulating in the subject has been reduced to 0.5 mg/L or less. In a further embodiment administration of the compound of Formula (I) is continued while a single dose of 200-2000 mg (preferably 250-1000 mg, more preferably 250-600 mg) of anti-SAP antibody is administered, and for 4-6 days thereafter. This constitutes a 'therapeutic course'—patients may require several courses to achieve the desired therapeutic effect. They are also likely to require intermittent repeat treatment. In one embodiment, the therapeutic course is repeated at least once at 3-6 week intervals as required. In a further embodiment, the therapeutic course is repeated at least once at 3-6 week intervals followed by at least one therapeutic course at 6-12 month intervals as required.

In a further aspect there is provided a method of treatment of a disease or disorder in a subject wherein SAP depletion would be beneficial, which method comprises administration of a therapeutically effective amount of the compound of Formula (I) in co-administration with an anti-SAP antibody.

In a further aspect there is provided a method of treatment of a disease or disorder in a subject wherein SAP depletion would be beneficial, which method comprises administration of a therapeutically effective amount of a pharmaceutical composition as herein described in co-administration with an anti-SAP antibody.

In a further aspect there is provided a method of depletion of SAP, which method comprises administration of a therapeutically effective amount of the compound of Formula (I) in co-administration with an anti-SAP antibody.

In a further aspect there is provided a method of depletion of SAP, which method comprises administration of a therapeutically effective amount of a pharmaceutical composition as herein described in co-administration with an anti-SAP antibody.

The invention further provides a method of treatment of a disease or disorder in a subject, wherein the disease or disorder is selected from the group consisting of amyloidosis, Alzheimer's disease, type 2 diabetes mellitus and osteoarthritis, which method comprises administering to the subject a therapeutically effective amount of a compound of Formula (I) in co-administration with an anti-SAP antibody.

The invention further provides a method of treatment of a disease or disorder in a subject, wherein the disease or disorder is selected from the group consisting of amyloidosis, Alzheimer's disease, type 2 diabetes mellitus and osteoarthritis, which method comprises administering to the subject a therapeutically effective amount of a pharmaceutical composition as herein described in co-administration with an anti-SAP antibody.

In another aspect, the invention provides for the compound of Formula (I) or one or more pharmaceutical compositions herein described in co-administration with an anti-SAP antibody for use in the treatment of a disease or disorder wherein SAP depletion would be beneficial.

In another aspect, the invention provides for the compound of Formula (I) or one or more pharmaceutical compositions herein described in co-administration with an anti-SAP antibody for use in the depletion of SAP.

In another aspect, the invention provides for the compound of Formula (I) in co-administration with an anti-SAP antibody for use in the treatment of a disease or disorder selected from the group consisting of amyloidosis, Alzheimer's disease, type 2 diabetes mellitus and osteoarthritis.

In another aspect, the invention provides for the compound of Formula (I) in co-administration with an anti-SAP antibody for use in the treatment of amyloidosis.

In one embodiment, the invention provides for the compound of Formula (I) in co-administration with an anti-SAP antibody for use in the treatment of systemic amyloidosis.

In one embodiment, the invention provides for the compound of Formula (I) in co-administration with an anti-SAP antibody for use in the treatment of AL-type amyloidosis.

In one embodiment, the invention provides for the compound of Formula (I) in co-administration with an anti-SAP antibody for use in the treatment of AA-type amyloidosis.

In one embodiment, the invention provides for the compound of Formula (I) in co-administration with an anti-SAP antibody for use in the treatment of dialysis amyloidosis.

In one embodiment, the invention provides for the compound of Formula (I) in co-administration with an anti-SAP antibody for use in the treatment of ATTR (transthyretin) amyloidosis.

In one embodiment, the invention provides for the compound of Formula (I) in co-administration with an anti-SAP antibody for use in the treatment of hereditary systemic amyloidosis.

In one embodiment, the invention provides for the compound of Formula (I) in co-administration with an anti-SAP antibody for use in the treatment of local amyloidosis.

In one embodiment, the invention provides for the compound of Formula (I) in co-administration with an anti-SAP antibody for use in the treatment of cerebral amyloid angiopathy.

In another aspect, the invention provides for a pharmaceutical composition as herein described in co-administration with an anti-SAP antibody for use in the treatment of a disease or disorder selected from the group consisting of amyloidosis, Alzheimer's disease, type 2 diabetes mellitus and osteoarthritis.

In another aspect, the invention provides for a pharmaceutical composition as herein described in co-administration with an anti-SAP antibody for use in the treatment of amyloidosis.

In one embodiment, the invention provides for a pharmaceutical composition as herein described in co-administration with an anti-SAP antibody for use in the treatment of systemic amyloidosis.

In one embodiment, the invention provides for a pharmaceutical composition as herein described in co-administration with an anti-SAP antibody for use in the treatment of AL-type amyloidosis.

In one embodiment, the invention provides for a pharmaceutical composition as herein described in co-administration with an anti-SAP antibody for use in the treatment of AA-type amyloidosis.

In one embodiment, the invention provides for a pharmaceutical composition as herein described in co-administration with an anti-SAP antibody for use in the treatment of dialysis amyloidosis.

In one embodiment, the invention provides for a pharmaceutical composition as herein described in co-administration with an anti-SAP antibody for use in the treatment of ATTR (transthyretin) amyloidosis.

In one embodiment, the invention provides for a pharmaceutical composition as herein described in co-administration with an anti-SAP antibody for use in the treatment of hereditary systemic amyloidosis.

In one embodiment, the invention provides for a pharmaceutical composition as herein described in co-administration with an anti-SAP antibody for use in the treatment of local amyloidosis.

In one embodiment, the invention provides for a pharmaceutical composition as herein described in co-administration with an anti-SAP antibody for use in the treatment of cerebral amyloid angiopathy.

In another aspect, the invention provides for the use of a compound of Formula (I) or a pharmaceutical composition as herein described in co-administration with an anti-SAP antibody in the treatment of a disease or disorder wherein SAP depletion would be beneficial.

In another aspect, the invention provides for the use of a compound of Formula (I) or a pharmaceutical composition as herein described in co-administration with an anti-SAP antibody for use in the depletion of SAP.

In another aspect, the invention provides for the use of a compound of Formula (I) in co-administration with an anti-SAP antibody in the treatment of a disease or disorder selected from the group consisting of amyloidosis, Alzheimer's disease, type 2 diabetes mellitus and osteoarthritis.

In another aspect, the invention provides for the use of a compound of Formula (I) in co-administration with an anti-SAP antibody in the treatment of amyloidosis.

In one embodiment, the invention provides for the use of a compound of Formula (I) in co-administration with an anti-SAP antibody in the treatment of systemic amyloidosis.

In one embodiment, the invention provides for the use of a compound of Formula (I) in co-administration with an anti-SAP antibody in the treatment of AL-type amyloidosis.

In one embodiment, the invention provides for the use of a compound of Formula (I) in co-administration with an anti-SAP antibody in the treatment of AA-type amyloidosis.

In one embodiment, the invention provides for the use of a compound of Formula (I) in co-administration with an anti-SAP antibody in the treatment of dialysis amyloidosis.

In one embodiment, the invention provides for the use of a compound of Formula (I) in co-administration with an anti-SAP antibody in the treatment of ATTR (transthyretin) amyloidosis.

In one embodiment, the invention provides for the use of a compound of Formula (I) in co-administration with an anti-SAP antibody in the treatment of hereditary systemic amyloidosis.

In one embodiment, the invention provides for the use of a compound of Formula (I) in co-administration with an anti-SAP antibody in the treatment of local amyloidosis.

In one embodiment, the invention provides for the use of a compound of Formula (I) in co-administration with an anti-SAP antibody in the treatment of cerebral amyloid angiopathy.

In another aspect, the invention provides for the use of a pharmaceutical composition as herein described in co-administration with an anti-SAP antibody in the treatment of a disease or disorder selected from the group consisting of amyloidosis, Alzheimer's disease, type 2 diabetes mellitus and osteoarthritis.

In another aspect, the invention provides for the use of a pharmaceutical composition as herein described in co-administration with an anti-SAP antibody in the treatment of amyloidosis.

In one embodiment, the invention provides for the use of a pharmaceutical composition as herein described in co-administration with an anti-SAP antibody in the treatment of systemic amyloidosis.

In one embodiment, the invention provides for the use of a pharmaceutical composition as herein described in co-administration with an anti-SAP antibody in the treatment of AL-type amyloidosis.

In one embodiment, the invention provides for the use of a pharmaceutical composition as herein described in co-administration with an anti-SAP antibody in the treatment of AA-type amyloidosis.

In one embodiment, the invention provides for the use of a pharmaceutical composition as herein described in co-administration with an anti-SAP antibody in the treatment of dialysis amyloidosis.

In one embodiment, the invention provides for the use of a pharmaceutical composition as herein described in co-administration with an anti-SAP antibody in the treatment of ATTR (transthyretin) amyloidosis.

In one embodiment, the invention provides for the use of a pharmaceutical composition as herein described in co-administration with an anti-SAP antibody in the treatment of hereditary systemic amyloidosis.

In one embodiment, the invention provides for the use of a pharmaceutical composition as herein described in co-administration with an anti-SAP antibody in the treatment of local amyloidosis.

In one embodiment, the invention provides for the use of a pharmaceutical composition as herein described in co-administration with an anti-SAP antibody in the treatment of cerebral amyloid angiopathy.

In another aspect, the invention provides for the use of a compound of Formula (I) and an anti-SAP antibody in the manufacture of a medicament for use in the treatment of a disease or disorder wherein SAP depletion would be beneficial.

In another aspect, the invention provides for the use of a compound of Formula (I) and an anti-SAP antibody in the manufacture of a medicament for use in the depletion of SAP.

In another aspect, the invention provides for the use of a compound of Formula (I) and an anti-SAP antibody in the manufacture of a medicament for use in the treatment of a disease or disorder selected from the group consisting of amyloidosis, Alzheimer's disease, type 2 diabetes mellitus and osteoarthritis.

In another aspect, the invention provides for the use of a compound of Formula (I) and an anti-SAP antibody in the manufacture of a medicament for use in the treatment of amyloidosis.

In one embodiment, the invention provides for the use of a compound of Formula (I) and an anti-SAP antibody in the manufacture of a medicament for use in the treatment of systemic amyloidosis.

In one embodiment, the invention provides for the use of a compound of Formula (I) and an anti-SAP antibody in the manufacture of a medicament for use in the treatment of AL-type amyloidosis.

In one embodiment, the invention provides for the use of a compound of Formula (I) and an anti-SAP antibody in the manufacture of a medicament for use in the treatment of AA-type amyloidosis.

In one embodiment, the invention provides for the use of a compound of Formula (I) and an anti-SAP antibody in the manufacture of a medicament for use in the treatment of dialysis amyloidosis.

In one embodiment, the invention provides for the use of a compound of Formula (I) and an anti-SAP antibody in the manufacture of a medicament for use in the treatment of ATTR (transthyretin) amyloidosis.

In one embodiment, the invention provides for the use of a compound of Formula (I) and an anti-SAP antibody in the manufacture of a medicament for use in the treatment of hereditary systemic amyloidosis.

In one embodiment, the invention provides for the use of a compound of Formula (I) and an anti-SAP antibody in the manufacture of a medicament for use in the treatment of local amyloidosis.

In one embodiment, the invention provides for the use of a compound of Formula (I) and an anti-SAP antibody in the manufacture of a medicament for use in the treatment of cerebral amyloid angiopathy.

In one embodiment the disease or disorder is amyloidosis.

In a further embodiment the disease or disorder is systemic amyloidosis.

In a further embodiment the disease or disorder is AL-type amyloidosis.

In a further embodiment the disease or disorder is AA-type amyloidosis.

In a further embodiment the disease or disorder is dialysis amyloidosis.

In a further embodiment the disease or disorder is ATTR (transthyretin) amyloidosis.

In a further embodiment the disease or disorder is hereditary systemic amyloidosis.

In another embodiment the disease or disorder is local amyloidosis.

In a further embodiment the disease or disorder is cerebral amyloid angiopathy.

In one embodiment the disease or disorder is Alzheimer's disease.

In one embodiment the disease or disorder is type 2 diabetes mellitus.

In one embodiment the disease or disorder is osteoarthritis.

In another embodiment of the invention, an article of manufacture, or "kit of parts", containing one or more unit doses of an anti-SAP antibody and one or more unit doses of the compound of Formula (I), useful for the treatment of amyloidosis, is provided.

In one embodiment the kit of parts comprises a unit dose of an anti-SAP antibody and one or more unit doses of the compound of Formula (I).

Suitably the kit of parts is formulated for the separate or sequential administration of the one or more unit doses of compound of Formula (I) and the unit dose of the anti-SAP antibody.

In one embodiment, the kit of parts comprises a container comprising one or more unit doses of the compound of Formula (I) or a pharmaceutical composition as herein described and the unit dose of the anti-SAP antibody.

In another embodiment, the kit of parts comprises a first container comprising one or more unit doses of the compound of Formula (I) or a pharmaceutical composition as herein described and a second container comprising the unit dose of the anti-SAP antibody.

The kit of parts may further comprise directions for the administration of the one or more unit doses of compound of Formula (I) and the unit dose of the anti-SAP antibody for treating or preventing amyloidosis.

In an alternative embodiment of the invention, an article of manufacture, or "kit of parts", containing one or more unit doses of the compound of Formula (I) or a pharmaceutical composition as herein described and one or more unit doses of a DNA vaccine is provided.

Suitable containers include, for example, bottles, vials, syringes and blister packs, etc.

WO2011/139917 discloses anti-transthyretin (anti-TTR) antisense oligonucleotides potentially useful in the modulation of expression of transthyretin and in treating, preventing, delaying or ameliorating transthyretin amyloidosis.

In another aspect, the invention provides for a method of treatment of ATTR (transthyretin) amyloidosis, which method comprises i) administering to a subject a therapeutically effective amount of a compound of formula (I) or a pharmaceutical composition as herein described in co-administration with an anti-SAP antibody, and ii) administering to a subject a therapeutically effective amount of an anti-TTR antisense oligonucleotide.

In one embodiment of the invention, the anti-TTR antisense oligonucleotide is ISIS 420915.

In one embodiment, steps i) and ii) are carried out sequentially.

In one embodiment, step ii) is carried out after step i).

WO2009040405 discloses agents for stabilising the tetrameric form of transthyretin useful in the treatment or prevention of transthyretin amyloidosis.

Therefore, in another aspect, the invention provides for a method of treatment of ATTR (transthyretin) amyloidosis, which method comprises i) administering to a subject a therapeutically effective amount of a compound of formula (I) or a pharmaceutical composition as herein described in co-administration with an anti-SAP antibody, and ii) administering to a subject a therapeutically effective amount of an agent as described in WO2009040405.

In one embodiment, steps i) and ii) are carried out sequentially.

In one embodiment, step ii) is carried out after step i).

The compound of Formula (I) may be synthesised substantially according to Reaction Scheme 1.

The compounds of Formula (I) can be prepared by reaction of the chloromethyl carbonate of Formula (II) with CPHPC in the presence of a solvent (e.g. dioxane), a base (e.g. potassium carbonate) and catalytic amounts of TBAI (tetrabutylammonium iodide).

The chloromethyl carbonate of Formula (II) can be prepared by reaction of chloromethyl carbonochloridate with tetrahydro-2H-pyran-4-ol in the presence of a solvent (e.g. diethyl ether or dichloromethane) and a base (e.g. pyridine or dimethylaminopyridine).

Chloromethyl carbonochloridate (also known as chloromethyl chloroformate) and tetrahydro-2H-pyran-4-ol are commercially available (Aldrich).

Reaction Scheme 1

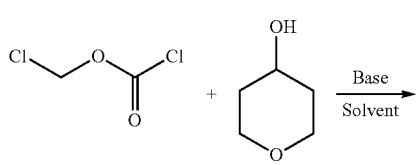

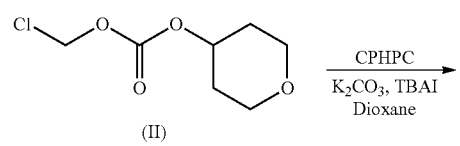

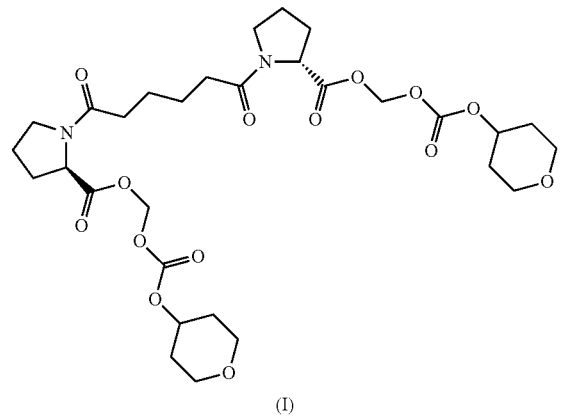

Alternatively, the compounds of Formula (I) can be synthesised substantially according to Reaction Scheme 2 starting from D-proline ((R)-pyrrolidine-2-carboxylic acid).

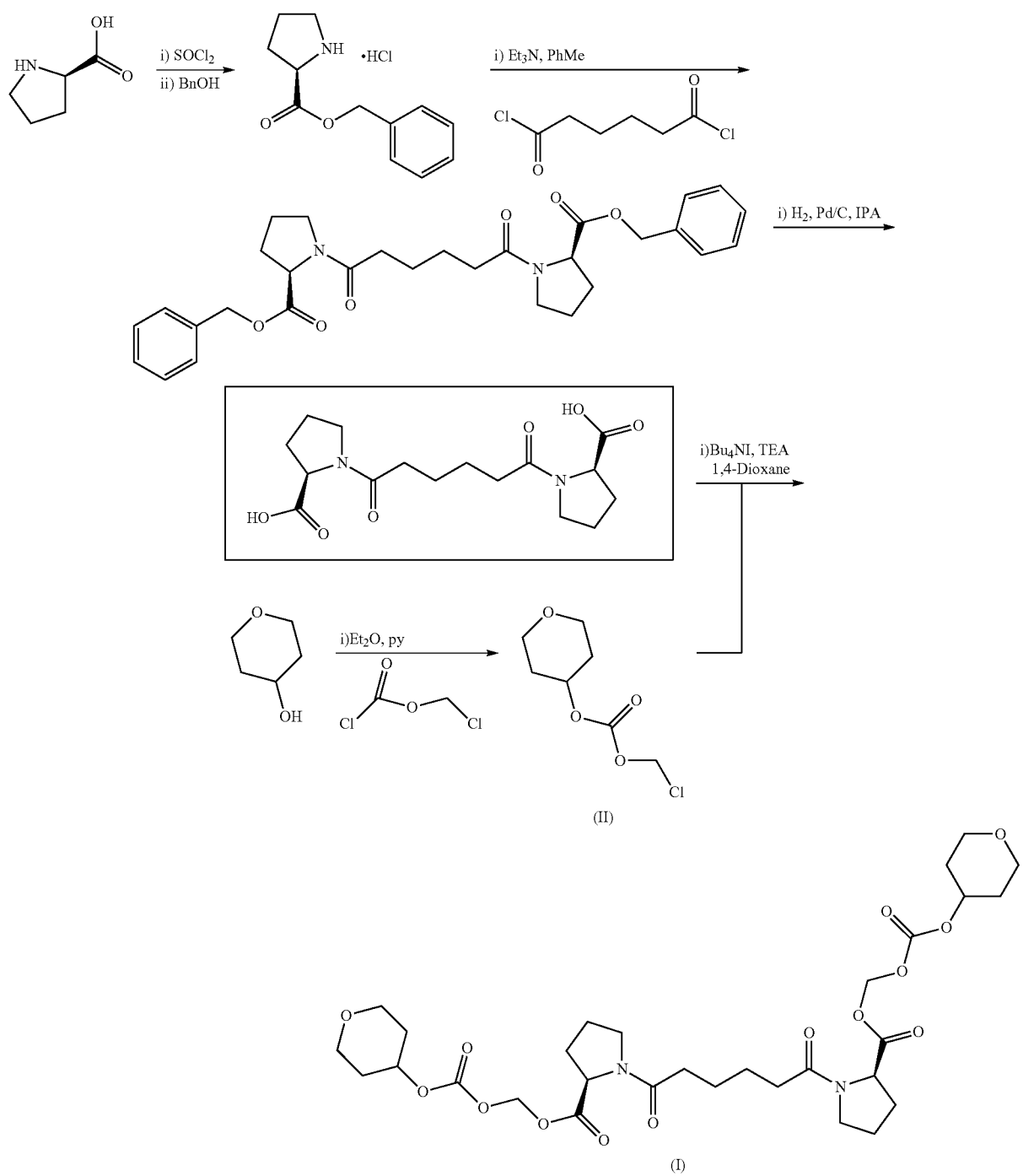

(II)

(I)

The compound in the box is CPHPC.
D-proline is commercially available (Aldrich).

EXAMPLES

The following Example illustrates the invention. This Example is not intended to limit the scope of the present invention, but rather to provide guidance to the skilled artisan to prepare and use the compound, compositions, and methods of the present invention. While particular embodiments of the present invention are described, the skilled artisan will appreciate that various changes and modifications can be made without departing from the spirit and scope of the invention.

All publications, including but not limited to patents and patent applications, cited in this specification are herein incorporated by reference as if each individual publication were specifically and individually indicated to be incorporated by reference herein as though fully set forth.

The following Intermediates and Examples illustrate the preparation of the compound of the invention.

Abbreviations
2-MeTHF 2-methyltetrahydrofuran
aq. aqueous
BnOH benzyl alcohol
Bu₄NI tetrabutylammonium iodide
DCM dichloromethane/methylene chloride
DMAP dimethylaminopyridine
ESI electrospray ionisation
EtOAc ethyl acetate
Et₂O diethyl ether
h hour
HCl hydrogen chloride/hydrochloric acid
HPLC high performance liquid chromatography
IPA isopropyl alcohol
$^i$Pr₂O isopropyl ether
MeCN/CH₃CN acetonitrile
Min minute
MS mass spectrometry
Na₂SO₄ sodium sulphate
NMR nuclear magnetic resonance
PhMe toluene
py pyridine
RT room temperature
TBAI tetrabutylammonium iodide
TEA triethylamine
TOF time of flight
THF tetrahydrofuran $^1$H and $^{13}$C NMR spectra were recorded on a Bruker 300 or 400 MHz. Chemical shifts are reported in parts per million (ppm, units). High-resolution mass spectra were recorded on a Micromass LCT (TOF) spectrometer coupled to analytical high performance liquid chromatography (HPLC). HPLC was conducted on a Waters X-Terra MS C18 column (3.5 μm 30×4.6 mm id) eluting with 0.01M ammonium acetate in water (solvent A) and 100% acetonitrile (solvent B), using the following elution gradient 0-0.5 minutes 5% B, 0.5-3.75 minutes 5% to 100% B, 3.75-4.5 100% B, 4.5-5 100% to 5% B, 5-5.5 5% B at a flow rate of 1.3 ml/minute at 40° C. The mass spectra (MS) were recorded on a Waters LCT mass spectrometer using electrospray positive ionisation [ES⁺ve to give MH⁺ molecular ions] or electrospray negative ionisation [ES-ve to give (M–H)⁻ molecular ions] modes.

Analytical HPLC was conducted on a XSelect XP C18 column (2.5 μm 30×4.6 mm id) eluting with 0.1% formic acid in water (solvent A) and 0.1% formic acid in acetonitrile (solvent B), using the following elution gradient 0-3.2 minutes: 5% to 100% B, 3.2-4.0 minutes 100% B, at a flow rate of 1.8 ml/minute at 40° C. The mass spectra (MS) were recorded on a Waters ZQ mass spectrometer using electrospray positive ionisation [ES⁺ to give MH⁺ molecular ions] or electrospray negative ionisation [ES⁻ to give (M–H)⁻ molecular ions] modes.

Intermediate 1: Chloromethyl (tetrahydro-2H-pyran-4-yl) carbonate

To a solution of tetrahydro-2H-pyran-4-ol (40 g, 392 mmol) in diethyl ether (500 mL) was added pyridine (38.0 mL, 470 mmol) and the solution was cooled to 0° C. Chloromethyl carbonochloridate (41.8 mL, 470 mmol) was added dropwise leading to the formation of a white solid. The reaction mixture was stirred at RT for 18 h. The reaction mixture was washed with water (200 mL), with HCl 0.5N (200 mL), and then with a saturated solution of NaHCO₃ (200 mL). The organic phase was dried over Na₂SO₄ and concentrated under reduced pressure.

Toluene was added and the solution was concentrated under reduced pressure (to remove chloromethyl carbonochloridate in excess). Chloromethyl (tetrahydro-2H-pyran-4-yl) carbonate (Intermediate 1) was obtained as a colourless oil (70 g, 360 mmol, 92% yield).

$^1$H NMR (400 MHz, CDCl₃) δ ppm 5.75 (s, 2H), 4.92 (m, 1H), 3.95 (m, 2H), 3.56 (m, 2H), 2.02 (m, 2H), 1.80 (m, 2H).

Intermediate 1 (Alternative preparation): Chloromethyl (tetrahydro-2H-pyran-4-yl) carbonate To a solution of chloromethyl carbonochloridate (5 g, 38.8 mmol) in DCM (50 mL) was added tetrahydro-2H-pyran-4-ol (3.96 g, 38.8 mmol) and the solution was cooled to 0° C. DMAP (4.97 g, 40.7 mmol) was added then the reaction mixture was stirred at RT for 18 h. The reaction mixture was diluted with water and extracted with DCM (3×100 mL). The organic phases were combined, dried over Na₂SO₄ and concentrated under reduced pressure. The pale yellow oil was purified by chromatography eluting with 10% EtOAc in cyclohexane. The appropriate fractions were combined and concentrated in vacuo to give the required product as a colorless oil (2.2 g, 11.3 mmol, 29.2% yield).

$^1$H NMR (300 MHz, CDCl₃) δ ppm 5.76 (s, 2H), 4.92 (m, 1H), 3.94 (m, 2H), 3.57 (m, 2H), 2.02 (m, 2H), 1.80 (m, 2H).

Example 1

(2R,2'R)-Bis(((((tetrahydro-2H-pyran-4-yl)oxy)carbonyl)oxy)methyl) 1,1'-adipoylbis(pyrrolidine-2-carboxylate)

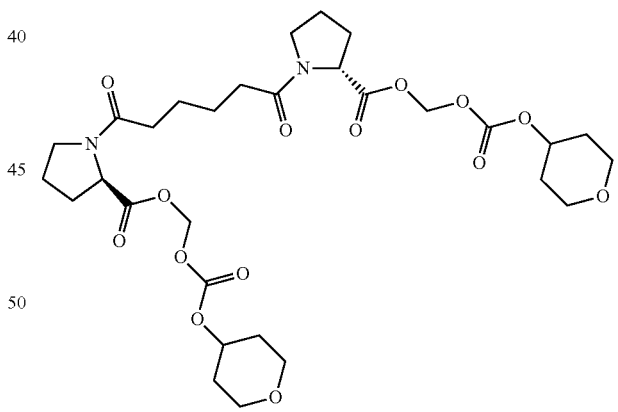

Solution A: Potassium carbonate (29.8 g, 216 mmol) was added to a stirred suspension of (2R,2'R)-1,1'-adipoylbis(pyrrolidine-2-carboxylic acid) (35 g, 103 mmol) in 1,4-dioxane (1 L) and the reaction mixture was stirred at 80° C. for 30 min.

Solution B: TBAI (7.60 g, 20.57 mmol) was added to a solution of chloromethyl (tetrahydro-2H-pyran-4-yl) carbonate (42.0 g, 216 mmol) in dioxane (50 mL) and the mixture was stirred at RT for 15 min.

The solution B was added to the solution A. The reaction mixture was stirred at 80° C. for 18 h.

The reaction mixture was filtered and concentrated under reduced pressure. The residue was taken up in EtOAc (400 mL) and washed with an aq. solution of NaHCO$_3$ (2×100 mL), an aq. solution of sodium thiosulfate (50 mL) and with 0.5N HCl (100 mL). The organic layer was dried over anhydrous Na$_2$SO$_4$, filtered and concentrated in vacuo. The yellow oil was solubilized in 2-MeTHF (100 mL) and sonicated until crystallization occurred. The mixture was left to stand for 1 h at RT. The precipitate was filtered and washed with a mixture 2-MeTHF/iPr$_2$O 70/30 to afford (2R,2'R)-bis(((((tetrahydro-2H-pyran-4-yl)oxy)carbonyl)oxy)methyl) 1,1'-adipoylbis(pyrrolidine-2-carboxylate) (Example 1) as an off white powder (42 g, 64.0 mmol, 62.2% yield). The product was dried under reduced pressure (5 mbar) and 35° C. for 12 h.

$^1$H NMR (400 MHz, CDCl$_3$) δ ppm 5.88 (d, J=5.5 Hz, 2H), 5.73 (d, J=5.5 Hz, 2H), 4.87 (m, 2H), 4.50 (m, 2H), 3.93 (m, 4H), 3.65 (m, 2H), 3.55 (m, 6H), 2.42-1.90 (m, 16H), 1.84-1.60 (m, 8H).

Some minor peaks were observed due to the presence of rotamers.

Recrystallisation of (2R,2'R)-bis(((((tetrahydro-2H-pyran-4-yl)oxy)carbonyl)oxy)methyl) 1,1-adipoylbis(pyrrolidine-2-carboxylate)

(2R,2'R)-bis(((((tetrahydro-2H-pyran-4-yl)oxy)carbonyl)oxy)methyl) 1,1'-adipoylbis(pyrrolidine-2-carboxylate) (170 g, 259 mmol) was suspended in 2-MeTHF and heated to 90° C. until complete dissolution. The solution was filtered when still hot and allowed to cool to RT. The precipitate was filtered and washed with a mixture of 2-MeTHF/iPr$_2$O 70/30 to afford (2R,2'R)-bis(((((tetrahydro-2H-pyran-4-yl)oxy)carbonyl)oxy)methyl) 1,1'-adipoylbis(pyrrolidine-2-carboxylate) (130 g, 198 mmol, 76% yield) as an off white crystalline solid. The product was dried under reduced pressure (5 mbar) and 35° C. for 24 h.

LC/MS: m/z 657 [M+H]$^+$, Rt 1.98 min.

$^1$H NMR (400 MHz, CDCl$_3$) δ ppm 5.87 (d, J=5.5 Hz, 2H), 5.71 (d, J=5.5 Hz, 2H), 4.86 (m, 2H), 4.49 (m, 2H), 3.91 (m, 4H), 3.63 (m, 2H), 3.54 (m, 6H), 2.43-1.85 (m, 16H), 1.84-1.59 (m, 8H).

Some minor peaks were observed due to the presence of rotamers.

$^{13}$C NMR (100 MHz, CDCl$_3$) 171.69, 170.85, 153.12, 82.26, 77.36, 77.05, 76.72, 73.94, 65.02, 58.41, 46.95, 34.11, 31.47, 29.02, 24.80, 24.17.

HRMS: m/z calculated for C$_{30}$H$_{45}$N$_2$O$_{14}$ [M+H]$^+$ 657.2870. found 657.2883.

XRPD data were acquired on a PANalytical X'Pert Pro powder diffractometer, model PW3040/60 using an X'Celerator detector. The acquisition conditions were: radiation: Cu Kα, generator tension: 40 kV, generator current: 45 mA, start angle: 2.0° 2θ, end angle: 40.0° 2θ, step size: 0.0167° 2θ, time per step: 31.75 seconds. The sample was prepared by mounting a few milligrams of sample (compound of Formula (I)) on a silicon wafer (zero background plate), resulting in a thin layer of powder.

The XRPD spectrum of the crystalline solid form of compound of Formula (I) is presented in FIG. 1. Characteristic XRPD angles and d-spacings for the compound of Formula (I) are recorded in Table 1. The margin of error is approximately ±0.1° 2θ for each of the peak assignments. Peak intensities may vary from sample to sample due to preferred orientation.

Peak positions were measured using Highscore software.

TABLE 1

XRPD diffraction angles and d-spacings for compound of Formula (I) Compound of formula (I)

| 2θ/° | d-spacings/Å |
|---|---|
| 3.6 | 24.4 |
| 7.2 | 12.3 |
| 10.8 | 8.2 |
| 14.4 | 6.2 |
| 16.1 | 5.5 |
| 17.1 | 5.2 |
| 18.0 | 4.9 |
| 18.5 | 4.8 |
| 19.8 | 4.5 |
| 21.7 | 4.1 |
| 22.9 | 3.9 |
| 24.3 | 3.7 |
| 27.1 | 3.3 |

In a further aspect, the invention provides for a compound of Formula (I) in crystalline form.

In a further aspect, the invention provides for a compound of Formula (I) as a crystalline solid characterised by an XRPD spectrum that is substantially as shown in FIG. 1.

In a further aspect, the invention provides for a compound of Formula (I) as a crystalline solid characterised by an XRPD spectrum comprising the peaks of Table 1.

Comparator Compounds

The data hereinafter reported compares the compound of Formula (I) with (2R,2'R)-bis(1-(pivaloyloxy)ethyl) 1,1'-adipoylbis(pyrrolidine-2-carboxylate) (Comparator Compound).

(2R,2'R)-bis(1-(pivaloyloxy)ethyl) 1,1'-adipoylbis(pyrrolidine-2-carboxylate) (also known as (R)-1-(6-{(R)-2-[1-(2,2-dimethyl-propionyloxy)-ethoxycarbonyl]-pyrrolidin-1-yl}-6-oxo-hexanoyl)-pyrrolidine-2-carboxylic acid 1-(2,2-dimethyl-propionyloxy)-ethyl ester) can be synthesised according to the experimental protocol disclosed in WO2003/051836.

Physicochemical Properties

Physical Form

The compound of Formula (I) is obtainable as a crystalline solid. By contrast, Comparator Compound is obtained as an oil (see WO2003/051836).

Solubility

Protocol for Determining Solubility

A known quantity of the compound of Formula (I) was weighed into a suitable vessel (e.g. a screw capped clear glass vial) and a known volume of the required media added (e.g. Simulated Gastric Fluid pH 1.6[SGF], Simulated Fed State Intestinal Fluid pH 6.5 [FeSSIF], Simulated Fasted State Intestinal Fluid pH 6.5 [FaSSIF], Water [Purified Water], or Britton-Robinson buffer). The compound was wetted with the media by vortex mixing for 30 seconds to 1 minute. The sample was then visually observed to ensure that undissolved solid remained present. The sample was transferred to a gentle mixer (such as a roller mixer) and allowed to agitate until the desired time point was reached. At appropriate times the sample was reassessed visually. If all the solid had dissolved the solubility was recorded as >x mg/ml where x is the known weight used divided by the volume added. If undissolved solid remained a portion of the sample was taken and centrifuged to remove the solid leaving a clear supernatant. The supernatant was diluted volumetrically with a suitable diluent to provide an analytical sample of suitable concentration for analysis. This diluted sample was then analysed by a suitable method such as HPLC against a standard(s) of known concentration. The solubility of the compound can then be calculated using a knowledge of the concentration of the standard, the relative response (e.g. peak areas) of the standard and the analytical sample described, and the dilution of the analytical sample.

The solubility of the compound of Formula (I) in various aqueous media are shown below in Table 2.

TABLE 2

Solubility of compound of Formula (I) in water, FeSSIF, FaSSIF and SGF at 4 hour timepoint

| Media Tested | Solubility (mg/ml) at 4 hour timepoint |
|---|---|
| SGF | 5.2 |
| FaSSIF | 4.4 |
| FeSSIF | 5.0 |
| Water | 5.5 |

Therefore the compound of Formula (I) is highly soluble in biologically relevant media.

Cytochrome p450 and Drug-Drug Interactions

The compound of Formula (I) and Comparator Compound were assessed in the cytochrome p450 (CYP 450) assay below. The results are shown below in Table 3.

The assay was designed to evaluate inhibition on cytochrome P450 (CYP) 3A4, 2C9, 2C19, 1A2 and 2D6 enzymes from bactosomes source using fluorogenic substrates. Compound (compound of Formula (I) or Comparator Compound) was dissolved in methanol at 1.65 mM. Daughter solutions were prepared in methanol at 660, 264, 106, 42, 17, 6.8, 2.7, 1.1 and 0.43 µM. NADPH cofactor was prepared with Glucose-6-phosphate (7.8 mg), Glucose-6-phosphate dehydrogenase (6 units), NADP (1.7 mg) per 1 mL in NaHCO$_3$ 2%.

Substrate preparation was as follows:
7-Methoxy-4-triFluoromethyl Coumarin-3-Acetic acid ethyl ester (FCA): 12.5 mM in acetonitrile
EthoxyResorufin (ER): 0.05 mM in acetonitrile
4-MethylaminoMethyl-7-Methoxy Coumarin (MMC): 2.5 mM in methanol
3-Butyryl-7Methoxy Coumarin (BMC): 2.5 mM in DMSO
7-BenzyloxyQuinoline (7BQ): 2.5 mM in acetonitrile
DiEthoxyFluorescein (DEF): 0.1 mM in acetonitrile Bactosomes (Cypex source) at the concentration of 10 mg of protein per ml were diluted in phosphate buffer 50 mM pH7.4:
0.33 ml of bactosomes CYP2C9 with 23.8 ml of buffer and 0.11 ml of FCA
0.33 ml of bactosomes CYP1A2 with 23.6 ml of buffer and 0.275 ml of ER
0.33 ml of bactosomes CYP2D6 with 23.8 ml of buffer and 0.11 ml of MMC
0.33 ml of bactosomes CYP2C19 with 23.8 ml of buffer and 0.11 ml of BMC
0.33 ml of bactosomes CYP3A4H with 23.6 ml of buffer and 0.275 ml of 7BQ
0.33 ml of bactosomes CYP3A4L with 23.6 ml of buffer and 0.275 ml of DEF Pre-Incubation consisted in mixing 5 µl of compound solution with 220 µl diluted bactosomes and warming it at 37° C. for 10 min. Incubation was started with the addition of 25 µl of NADPH. Then fluorescence of substrate metabolite was read in a SAFIRE instrument (from Tecan) for 5 min:

FCA (2C9): Excitation at 410 nm and Emission at 510 nm
ER (1A2): Excitation at 530 nm and Emission at 590 nm
MMC (2D6): Excitation at 410 nm and Emission at 485 nm
BMC (2C19): Excitation at 410 nm and Emission at 465 nm
7BQ (3A4H): Excitation at 410 nm and Emission at 530 nm
DEF (3A4L): Excitation at 485 nm and Emission at 530 nm Plotting of inhibition of substrate production against compound concentration allowed the determination of $IC_{50}$ values.

TABLE 3

Inhibition of cytochrome p450 enzymes by compound of Formula (I) (Example 1) and Comparator Compound.

| CYP450 enzyme | Compound of Formula (I) $IC_{50}$ (µM) | Comparator Compound $IC_{50}$ (µM) |
|---|---|---|
| CYP1A2 | >33 | >33 |
| CYP2C19 | >33 | >33 |
| CYP2C9 | >33 | 26 |
| CYP2D6 | >33 | >33 |
| CYP3A4 (7BQ) | >33 | 5.5 |
| CYP3A4 (DEF) | >33 | 1.1 |

In fluorescence based screening assays using recombinant human CYP 450, the compound of Formula (I) and its mono-ester derivative did not demonstrate significant inhibition of the major human liver cytochrome P450s (Cypex): CYP3A4-DEF and 3A4-7BQ with $IC_{50}$>33 µM. The other isoforms were also not significantly inhibited by both compounds with $IC_{50}$>33 µM). By contrast, Comparator Compound demonstrated significant inhibition of CYP3A4-DEF and CYP3A4-7BQ.

For a compound where the systemic concentration is going to be low, only CYP3A4 inhibition is relevant as only intestinal inhibition will be relevant (CYP3A is present in enterocytes and is responsible for enterocyte first pass).

Physical Stability

Protocol for Determining Physical Stability:

The assay was designed for determining physical stability of compound in buffer at various pHs. Compound of Formula (I) was dissolved in DMSO at 1 mg/ml. Phosphate buffer (PBS) was prepared by mixing $K_2HPO_4$ 50 mM and $KH_2PO_4$ 50 mM solutions to obtain 4 buffers at pH 6.0, 7.0, 7.5, 8.0.

Stability studies were conducted at room temperature, and were started by the addition of 8 µl of DMSO solution to 792 µl of PBS 50 mM at pH 6.0, 7.0, 7.5 or 8.0 (1% DMSO). 75 µl of mixture was taken at 0, 1, 2, 4 and 24 h and 225 µl acetonitrile containing internal standard was added.

2 µl of samples were injected into the liquid chromatography system and eluted with a Ascentis C18 column (50×2.1 mm id, 2.7 µm) and with 0.1% formic acid in water (A) and 0.1% formic acid in acetonitrile (B), using the following elution 2 min gradient: 5 to 95% B over 1.2 min, 95% B over 0.6 min and 0.1 min for re-equilibrate column, at 0.5 mL/min at 50° C.

Samples were analysed by Mass Spectrometry with an electrospray source and in positive mode and with following mass transitions:

Compound of Formula (I): 657 to 384
Monoester of CPHPC: 499 to 226
CPHPC: 341 to 226

Figure 2:
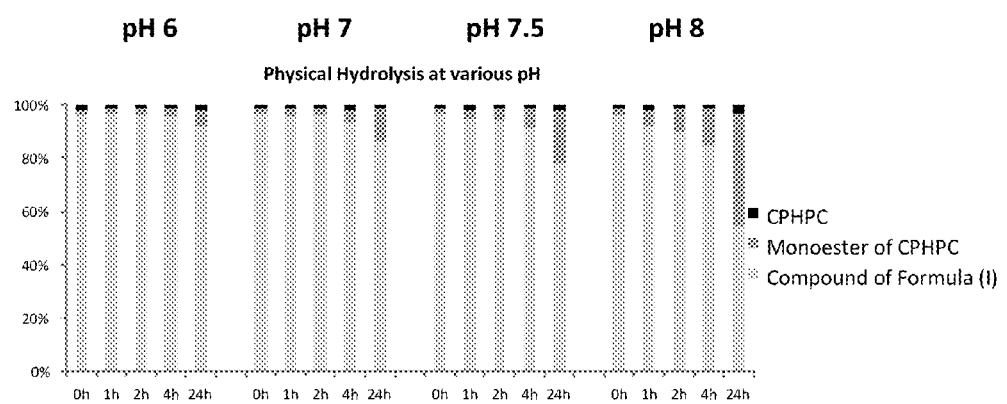
FIG. 2 shows in vitro physical hydrolysis of the compound of Formula (I) in phosphate buffered saline at pH 6, 7, 7.5 and 8.

Data showing in vitro physical hydrolysis of the compound of Formula (I) in phosphate buffered saline at pH 6, 7, 7.5 and 8 at various time points is presented in FIG. 2.

By "monoester of CPHPC" is meant the compound (R)-1-(6-oxo-6-((R)-2-(((((tetrahydro-2H-pyran-4-yl)oxy)carbonyl)oxy)methoxy)carbonyl)pyrrolidin-1-yl)hexanoyl)pyrrolidine-2-carboxylic acid of Formula (III).

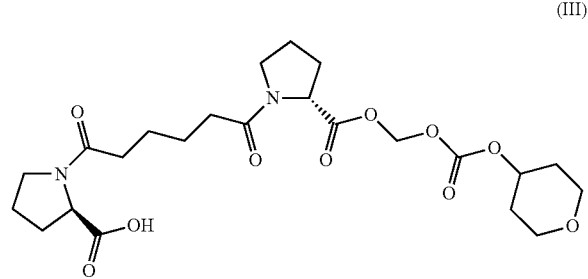 [SMILES: O=C(OCOC(=O)[C@H]1CCCN1C(=O)CCCCC(=O)N1CCC[C@@H]1C(=O)O)OC1CCOCC1]

(III)

The compound of Formula (I) seemed to be less sensitive to hydrolysis for a pH below 7.5. Less than 20% of the compound of Formula (I) was hydrolysed after 24 h in an acidic environment (pH less than 7.0).

Intestinal and Liver Microsomal Hydrolysis
Intestine and Liver Microsomal Assay Protocol The assay was designed for determining stability of compound in microsomal matrix. Compound (Compound of Formula (I)) was dissolved in DMSO at 1 mg/ml. Daughter solution was prepared in methanol/water (50/50) at 30.3 ng/ml. Microsomes (from Xenotech) were diluted at 0.625 mg proteins per ml in phosphate buffer 50 mM pH 7.4.

Pre-Incubation consisted of warming microsomal solution 395 µl with 100 µl NaHCO$_3$ (2%) at 37° C. for 7 min. Incubation was started with the addition of 5 µl of daughter solution. 50 µl aliquots of mixture were taken at 0, 3, 6, 12 and 30 min and quenched with 150 µl acetonitrile containing internal standard.

After 10 min centrifugation at 4000 rpm, 2 µl of samples were injected into the liquid chromatography system and eluted on a Ascentis C18 column (50×2.1 mm id, 2.7 µm) with 0.1% formic acid in water (A) and 0.1% formic acid in acetonitrile (B), using the following 2 minute elution gradient: 5 to 95% B over 1.2 min, 95% B over 0.6 min and 0.1 min for re-equilibrate column, at 0.5 mL/min at 50° C.

Samples were analysed by Mass Spectrometry with an electrospray source, in positive mode and with following mass transitions:

Compound of Formula (I): 657 to 384
Monoester of CPHPC: 499 to 226
CPHPC: 341 to 226

Controls were made to calculate percentage of disappearance of parent but also appearance of suspected metabolite, i.e. monoester and diacidic form.

Figure 3:
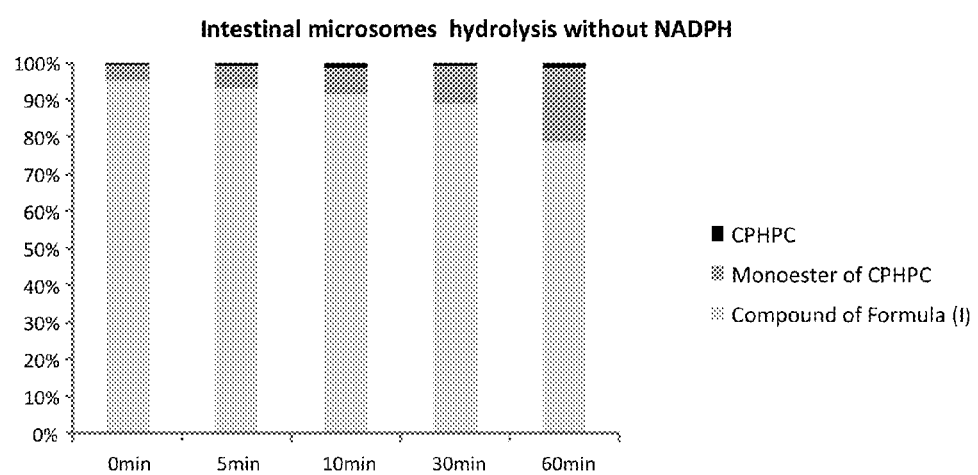
FIG. 3 shows in vitro Intestinal Microsomal Stability of the compound of Formula (I) in human microsomes.

Data showing in vitro Intestinal Microsomal Stability of Compound of Formula (I) in human microsomes is presented in FIG. 3. "0/5/10/30/60 min" refers to the time (in minutes) that the sample was taken from the mixture for analysis.

As can be seen from FIG. 3, the compound of Formula (I) exhibited a low rate of hydrolysis in human intestinal microsomes, even after 60 minutes, suggesting that the compound of Formula (I) will not be unduly unstable in the gut and so be available for absorption.

From the intestine, the compound of Formula (I) is transported through the intestinal wall and is transported to the bloodstream and liver, both sites of circulating SAP.

Protocol for Determining Blood Hydrolysis

The assay was designed for determining stability of compound in fresh blood. Compound (compound of Formula (I)) was dissolved in DMSO at 1 mg/ml. Daughter solution was prepared in DMSO at 100 µg/ml. Fresh blood was diluted 1/2 in isotonic buffer pH 7.4.

Pre-Incubation consisted of warming 792 µl of blood at 37° C. for 7 min. Incubations were started with the addition of 5 µl of daughter solution. 50 µl of mixture were taken at 0, 5, 15, 30 and 60 min. 50 µl of water was add to sample and then quenched with 300 µl acetonitrile containing internal standard.

After 10 min centrifugation at 4000 rpm, 2 µl of samples were injected into the liquid chromatography system and eluted with a Ascentis C18 column (50×2.1 mm id, 2.7 µm) and with 0.1% formic acid in water (A) and 0.1% formic acid in acetonitrile (B), using the following elution gradient over 2 minutes: 5 to 95% B over 1.2 min, 95% B over 0.6 min and 0.1 min for re-equilibrate column, at 0.5 mL/min at 50° C. Samples were analysed by Mass Spectrometry with an electrospray source, in positive mode and with following mass transitions:

Compound of Formula (I): 657 to 384
Monoester of CPHPC: 499 to 226
CPHPC: 341 to 226

Controls were made to calculate percentage of disappearance of parent but also apparition of suspected metabolite, i.e. monoester and diacidic form.

Figure 4:
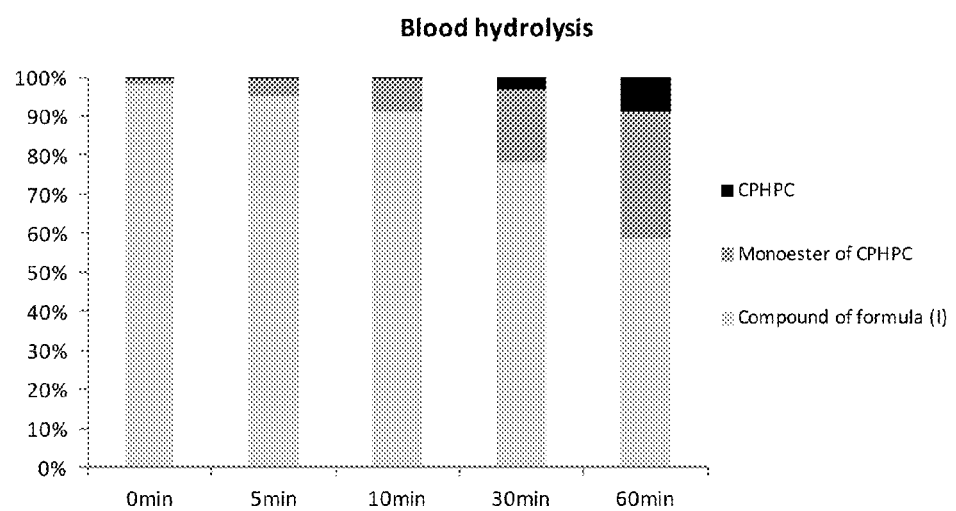
FIG. 4 shows in vitro Blood stability of the compound of Formula (I) in human blood.

Data showing in vitro Blood stability of compound of Formula (I) in human blood is presented in FIG. 4. "0/5/10/30/60 min" refers to the time (in minutes) that the sample was taken from the mixture for analysis.

In vitro liver microsomal activity of was assessed using the protocol detailed above (Intestine and Liver Microsomal Assay protocol).

Figure 5:
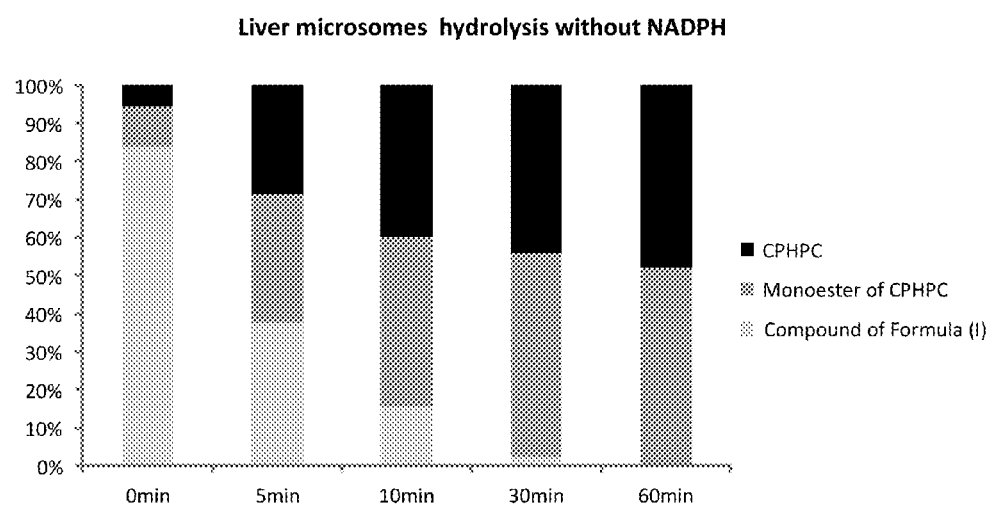
FIG. 5 shows in vitro Liver microsomal stability of the compound of Formula (I) in human liver microsomes.

Data showing in vitro Liver microsomal stability of compound of Formula (I) in human liver microsomes is presented in FIG. 5. "0/5/10/30/60 min" refers to the time (in minutes) that the sample was taken from the mixture for analysis.

In human liver microsomes, a high rate of hydrolysis of compound of Formula (I) to CPHPC was observed (approximately 50% conversion to CPHPC was achieved within 30 minutes), suggesting that compound of Formula (I) is capable of being cleaved to active CPHPC once absorbed.

REFERENCES

1. Tennent, G. A., Lovat, L. B. and Pepys, M. B. (1995) Serum amyloid P component prevents proteolysis of the amyloid fibrils of Alzheimer's disease and systemic amyloidosis. *Proc. Natl. Acad. Sci. USA,* 92: 4299-4303.
2. Botto, M., Hawkins, P. N., Bickerstaff, M. C. M., Herbert, J., Bygrave, A. E., McBride, A., Hutchinson, W. L., Tennent, G. A., Walport, M. J. and Pepys, M. B. (1997) Amyloid deposition is delayed in mice with targeted deletion of the serum amyloid P component gene. *Nature Med.,* 3: 855-859.
3. Hamazaki, H. (1995) Amyloid P component promotes aggregation of Alzheimer's b-amyloid peptide. *Biochem. Biophys. Res. Commun.,* 211: 349-353.

4. Myers, S. L., Jones, S., Jahn, T. R., Morten, I. J., Tennent, G. A., Hewitt, E. W. and Radford, S. E. (2006) A systematic study of the effect of physiological factors on b$_2$-microglobulin amyloid formation at neutral pH. *Biochemistry*, 45: 2311-2321.

5. Mold, M., Shrive, A. K. and Exley, C. (2012) Serum amyloid P component accelerates the formation and enhances the stability of amyloid fibrils in a physiologically significant under-saturated solution of amyloid-b$_{42}$. *Journal of Alzheimer's Disease*, 29: 875-881.

6. Pepys, M. B., Herbert, J., Hutchinson, W. L., Tennent, G. A., Lachmann, H. J., Gallimore, J. R., Lovat, L. B., Bartfai, T., Alanine, A., Hertel, C., Hoffmann, T., Jakob-Roetne, R., Norcross, R. D., Kemp, J. A., Yamamura, K., Suzuki, M., Taylor, G. W., Murray, S., Thompson, D., Purvis, A., Kolstoe, S., Wood, S. P. and Hawkins, P. N. (2002) Targeted pharmacological depletion of serum amyloid P component for treatment of human amyloidosis. *Nature*, 417: 254-259.

7. Gillmore, J. D., Tennent, G. A., Hutchinson, W. L., Gallimore, J. R., Lachmann, H. J., Goodman, H. J. B., Offer, M., Millar, D. J., Petrie, A., Hawkins, P. N. and Pepys, M. B. (2010) Sustained pharmacological depletion of serum amyloid P component in patients with systemic amyloidosis. *Br. J. Haematol.*, 148: 760-767.

8. Pepys, M. B. (2006) Amyloidosis. *Annu. Rev. Med.*, 57: 223-241.

9. Urbányi, Z., Lakics, V. and Erdó, S. L. (1994) Serum amyloid P component-induced cell death in primary cultures of rat cerebral cortex. *Eur. J. Pharmacol.*, 270: 375-387.

10. Duong, T., Acton, P. J. and Johnson, R. A. (1998) The in vitro neuronal toxicity of pentraxins associated with Alzheimer's disease brain lesions. *Brain Res.*, 813: 303-312.

11. Urbányi, Z., Laszlo, L., Tomasi, T. B., Toth, E., Mekes, E., Sass, M. and Pazmany, T. (2003) Serum amyloid P component induces neuronal apoptosis and beta-amyloid immunoreactivity. *Brain Res.*, 988: 69-77.

12. Urbányi, Z., Sass, M., Laszy, J., Takacs, V., Gyertyan, I. and Pazmany, T. (2007) Serum amyloid P component induces TUNEL-positive nuclei in rat brain after intrahippocampal administration. *Brain Res.*, 1145: 221-226.

13. Pisalyaput, K. and Tenner, A. J. (2008) Complement component C1q inhibits b-amyloid- and serum amyloid P-induced neurotoxicity via caspase- and calpain-independent mechanisms. *J. Neurochem.*, 104: 696-707.

14. Pepys, M. B., Gallimore, J. R., Lloyd, J., Li, Z., Graham, D., Taylor, G. W., Ellmerich, S., Mangione, P. P., Tennent, G. A., Hutchinson, W. L., Millar, D. J., Bennett, G., More, J., Evans, D., Mistry, Y., Poole, S. and Hawkins, P. N. (2012) Isolation and characterization of pharmaceutical grade human pentraxins, serum amyloid P component and C-reactive protein, for clinical use. *J. Immunol. Methods*, 384: 92-102.

15. Duong, T., Pommier, E. C. and Scheibel, A. B. (1989) Immunodetection of the amyloid P component in Alzheimer's disease. *Acta Neuropathol.*, 78: 429-437.

16. Kalaria, R. N., Galloway, P. G. and Perry, G. (1991) Widespread serum amyloid P immunoreactivity in cortical amyloid deposits and the neurofibrillary pathology of Alzheimer's disease and other degenerative disorders. *Neuropathol. Appl. Neurobiol.*, 17: 189-201.

17. Kalaria, R. N., Golde, T. E., Cohen, M. L. and Younkin, S. G. (1991) Serum amyloid P component in Alzheimer's disease. Implications for dysfunction of the blood-brain barrier. *Ann. N. Y. Acad. Sci.*, 640: 145-148.

18. Duong, T., Doucette, T., Zidenberg, N. A., Jacobs, R. W. and Scheibel, A. B. (1993) Microtubule-associated proteins tau and amyloid P component in Alzheimer's disease. *Brain Res.*, 603: 74-86.

19. Perlmutter, L. S., Barrón, E., Myers, M., Saperia, D. and Chui, H. C. (1995) Localization of amyloid P component in human brain: vascular staining patterns and association with Alzheimer's disease lesions. *J. Comp. Neurol.*, 352: 92-105.

20. Crawford, J. R., Bjorklund, N. L., Taglialatela, G. and Gomer, R. H. (2012) Brain serum amyloid P levels are reduced in individuals that lack dementia while having Alzheimer's disease neuropathology. *Neurochem. Res.*, 37: 795-801.

21. Kolstoe, S. E., Ridha, B. H., Bellotti, V., Wang, N., Robinson, C. V., Crutch, S. J., Keir, G., Kukkastenvehmas, R., Gallimore, J. R., Hutchinson, W. L., Hawkins, P. N., Wood, S. P., Rossor, M. N. and Pepys, M. B. (2009) Molecular dissection of Alzheimer's disease neuropathology by depletion of serum amyloid P component. *Proc. Natl. Acad. Sci. USA*, 106: 7619-7623.

22. Hawrylycz, M. J., Lein, E. S., Guillozet-Bongaarts, A. L., Shen, E. H., Ng, L., Miller, J. A., van de Lagemaat, L. N., Smith, K. A., Ebbert, A., Riley, Z. L., Abajian, C., Beckmann, C. F., Bernard, A., Bertagnolli, D., Boe, A. F., Cartagena, P. M., Chakravarty, M. M., Chapin, M., Chong, J., Dailey, R. A., Daly, B. D., Dang, C., Datta, S., Dee, N., Dolbeare, T. A., Faber, V., Feng, D., Fowler, D. R., Goldy, J., Gregor, B. W., Haradon, Z., Haynor, D. R., Hohmann, J. G., Horvath, S., Howard, R. E., Jeromin, A., Jochim, J. M., Kinnunen, M., Lau, C., Lazarz, E. T., Lee, C., Lemon, T. A., Li, L., Li, Y., Morris, J. A., Overly, C. C., Parker, P. D., Parry, S. E., Reding, M., Royall, J. J., Schulkin, J., Sequeira, P. A., Slaughterbeck, C. R., Smith, S. C., Sodt, A. J., Sunkin, S. M., Swanson, B. E., Vawter, M. P., Williams, D., Wohnoutka, P., Zielke, H. R., Geschwind, D. H., Hof, P. R., Smith, S. M., Koch, C., Grant, S. G. N. and Jones, A. R. (2012) An anatomically comprehensive atlas of the adult human brain transcriptome. *Nature*, 489: 391-399.

23. Pepys, M. B. and Butler, P. J. G. (1987) Serum amyloid P component is the major calcium-dependent specific DNA binding protein of the serum. *Biochem. Biophys. Res. Commun.*, 148: 308-313.

24. Butler, P. J. G., Tennent, G. A. and Pepys, M. B. (1990) Pentraxin-chromatin interactions: serum amyloid P component specifically displaces H1-type histones and solubilizes native long chromatin. *J. Exp. Med.*, 172: 13-18.

25. Wang, Y., Guo, Y., Wang, X., Huang, J., Shang, J. and Sun, S. (2011) Human serum amyloid P functions as a negative regulator of the innate and adaptive immune responses to DNA vaccines. *J. Immunol.*, 186: 2860-2870.

26. Wang, Y., Guo, Y., Wang, X., Huang, J., Shang, J. and Sun, S. (2011) Serum amyloid P component facilitates DNA clearance and inhibits plasmid transfection: implications for human DNA vaccine. *Gene Ther.*: [Epub ahead of print].

27. Noursadeghi, M., Bickerstaff, M. C. M., Gallimore, J. R., Herbert, J., Cohen, J. and Pepys, M. B. (2000) Role of serum amyloid P component in bacterial infection: protection of the host or protection of the pathogen. *Proc. Natl. Acad. Sci. USA*, 97: 14584-14589.

28. Gilchrist, K. B., Garcia, M. C., Sobonya, R., Lipke, P. N. and Klotz, S. A. (2012) New features of invasive candidiasis in humans: amyloid formation by fungi and deposition of serum amyloid P component by the host. *J Infect Dis*, 206(9): 1473-1478.

The invention claimed is:

1. A kit of parts comprising at least one dosage form of a compound which is (2R,2'R)-bis(((((tetrahydro-2H-pyran-4-yl)oxy)carbonyl)oxy)methyl) 1,1'-adipoylbis(pyrrolidine-2-carboxylate) according to Formula (I):

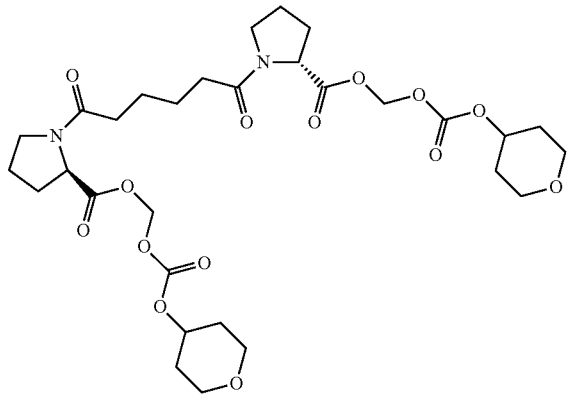

(I)

and at least one dosage form of an anti-SAP antibody wherein the amino acid sequence of the anti-SAP antibody comprises the heavy and light chain CDRs of SEQ ID NO:5, SEQ ID NO:6 and SEQ ID NO:7, SEQ ID NO:8, SEQ ID NO:9 and SEQ ID NO:10.

2. A method of alleviation of symptoms or retardation of progression of a disease or disorder in a subject wherein SAP depletion would be beneficial, selected from the group consisting of amyloidosis, Alzheimer's disease, type 2 diabetes mellitus, and osteoarthritis, which method comprises administration of a therapeutically effective amount of a compound which is (2R,2'R)-bis(((((tetrahydro-2H-pyran-4-yl)oxy)carbonyl)oxy)methyl) 1,1'-adipoylbis(pyrrolidine-2-carboxylate) according to Formula (I):

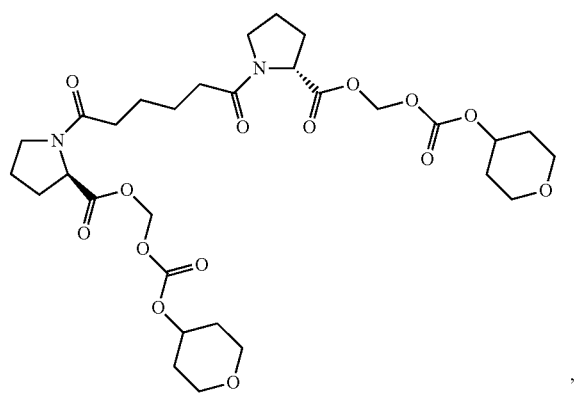

(I)

and an anti-SAP antibody wherein the amino acid sequence of the anti-SAP antibody comprises the heavy and light chain CDRs of SEQ ID NO:5, SEQ ID NO:6 and SEQ ID NO:7, SEQ ID NO:8, SEQ ID NO:9 and SEQ ID NO:10.

3. The method according to claim 2 wherein the disease or disorder is systemic amyloidosis.

4. The method according to claim 2 wherein the compound is administered prior to administration of the anti-SAP antibody.

5. The method according to claim 4 wherein the anti-SAP antibody is administered when the level of circulating SAP in the subject has been reduced to a level of less than 2 mg/L.

6. The method according to claim 4 wherein the anti-SAP antibody is administered when the level of circulating SAP in the subject has been reduced to a level of 1 mg/L or less.

7. The method according to claim 4 wherein the anti-SAP antibody is administered when the level of circulating SAP in the subject has been reduced to a level of 0.5 mg/L or less.

8. The method according to claim 4 wherein the compound is administered for 5-8 days or until the level of the SAP circulating in the subject has been reduced to a level of less than 2 mg/L whichever is longer.

9. The method according to claim 2 wherein the disease or disorder is amyloidosis.

10. The method according to claim 9 wherein the disease or disorder is ATTR amyloidosis.

11. The method according to claim 9 wherein the disease or disorder is cerebral amyloid angiopathy.

12. The method according to claim 9 wherein the compound is administered prior to administration of the anti-SAP antibody.

13. The method according to claim 12 wherein the anti-SAP antibody is administered when the level of circulating SAP in the subject has been reduced to a level of less than 2 mg/L.

14. The method according to claim 12 wherein the anti-SAP antibody is administered when the level of circulating SAP in the subject has been reduced to a level of 1 mg/L or less.

15. The method according to claim 12 wherein the anti-SAP antibody is administered when the level of circulating SAP in the subject has been reduced to a level of 0.5 mg/L or less.

16. The method according to claim 12 wherein the compound is administered for 5-8 days or until the level of the SAP circulating in the subject has been reduced to a level of less than 2 mg/L whichever is longer.

* * * * *

SEQUENCE LISTING

<160> NUMBER OF SEQ ID NOS: 10

<210> SEQ ID NO 1
<211> LENGTH: 120
<212> TYPE: PRT
<213> ORGANISM: Artificial Sequence
<220> FEATURE:
<223> OTHER INFORMATION: SAP-E humanised VH variant H1 amino acid
      sequence

<400> SEQUENCE: 1

Gln Val Gln Leu Val Gln Ser Gly Ala Glu Val Lys Lys Pro Gly Ser
 1               5                  10                  15

Ser Val Lys Val Ser Cys Lys Ala Ser Gly Phe Thr Phe Ala Thr Tyr
                20                  25                  30

Asn Met His Trp Val Arg Gln Ala Pro Gly Gln Gly Leu Glu Trp Met
            35                  40                  45

Gly Tyr Ile Tyr Pro Gly Asp Gly Asn Ala Asn Tyr Asn Gln Gln Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Arg Asp Phe Asp Tyr Asp Gly Gly Tyr Tyr Phe Asp Ser Trp Gly Gln
                100                 105                 110

Gly Thr Leu Val Thr Val Ser Ser
        115                 120

<210> SEQ ID NO 2
<211> LENGTH: 107
<212> TYPE: PRT
<213> ORGANISM: Artificial Sequence
<220> FEATURE:
<223> OTHER INFORMATION: SAP-E humanised VL variant L1 amino acid
      sequence

<400> SEQUENCE: 2

Asp Ile Gln Met Thr Gln Ser Pro Ser Ser Leu Ser Ala Ser Val Gly
 1               5                  10                  15

Asp Arg Val Thr Ile Thr Cys Arg Ala Ser Glu Asn Ile Tyr Ser Tyr
                20                  25                  30

Leu Ala Trp Tyr Gln Gln Lys Pro Gly Lys Ala Pro Lys Leu Leu Ile
            35                  40                  45

His Asn Ala Lys Thr Leu Ala Glu Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Ala Pro Leu
                85                  90                  95

Thr Phe Gly Gln Gly Thr Lys Leu Glu Ile Lys
                100                 105

<210> SEQ ID NO 3
<211> LENGTH: 444
<212> TYPE: PRT
<213> ORGANISM: Artificial Sequence
<220> FEATURE:
<223> OTHER INFORMATION: SAP-E humanised heavy chain H1 full mature
      amino acid sequence

<400> SEQUENCE: 3

-continued

```
Gln Val Gln Leu Val Gln Ser Gly Ala Glu Val Lys Lys Pro Gly Ser
  1               5                  10                  15

Ser Val Lys Val Ser Cys Lys Ala Ser Gly Phe Thr Phe Ala Thr Tyr
              20                  25                  30

Asn Met His Trp Val Arg Gln Ala Pro Gly Gln Gly Leu Glu Trp Met
          35                  40                  45

Gly Tyr Ile Tyr Pro Gly Asp Gly Asn Ala Asn Tyr Asn Gln Gln Phe
      50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
              85                  90                  95

Arg Asp Phe Asp Tyr Asp Gly Gly Tyr Tyr Phe Asp Ser Trp Gly Gln
             100                 105                 110

Gly Thr Leu Val Thr Val Ser Ser Ala Ser Thr Lys Gly Pro Ser Val
             115                 120                 125

Phe Pro Leu Ala Pro Ser Ser Lys Ser Thr Ser Gly Gly Thr Ala Ala
         130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                 165                 170                 175

Leu Gln Ser Ser Gly Ser Leu Ser Ser Val Val Thr Val Pro Ser Ser
             180                 185                 190

Ser Leu Gly Thr Gln Thr Tyr Ile Cys Asn Val Asn His Lys Pro Ser
             195                 200                 205

Asn Thr Lys Val Asp Lys Lys Val Glu Pro Lys Ser Cys Asp Lys Thr
         210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                 245                 250                 255

Thr Pro Glu Val Thr Cys Val Val Asp Val Ser His Glu Asp Pro
             260                 265                 270

Glu Val Lys Phe Asn Trp Tyr Val Asp Gly Val Glu Val His Asn Ala
             275                 280                 285

Lys Thr Lys Pro Arg Glu Glu Gln Tyr Asn Ser Tyr Val Val Ser Val
         290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                 325                 330                 335

Lys Ala Lys Gly Gln Pro Arg Glu Pro Gln Val Tyr Thr Leu Pro Pro
             340                 345                 350

Ser Arg Asp Glu Leu Thr Lys Asn Gln Val Ser Leu Thr Cys Leu Val
             355                 360                 365
```

```
Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Lys Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 4
<211> LENGTH: 214
<212> TYPE: PRT
<213> ORGANISM: Artificial Sequence
<220> FEATURE:
<223> OTHER INFORMATION: SAP-E humanised light chain L1 full mature
      amino acid sequence

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ala Pro Lys Leu Leu Ile
        35                  40                  45

His Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Ala Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 5
<211> LENGTH: 5
<212> TYPE: PRT
<213> ORGANISM: Mus musculus
<220> FEATURE:
<223> OTHER INFORMATION: SAP-E CDRH1 amino acid

<400> SEQUENCE: 5

Thr Tyr Asn Met His
```

-continued

```
<210> SEQ ID NO 6
<211> LENGTH: 17
<212> TYPE: PRT
<213> ORGANISM: Mus musculus
<220> FEATURE:
<223> OTHER INFORMATION: SAP-E CDRH2 amino acid

<400> SEQUENCE: 6

Tyr Ile Tyr Pro Gly Asp Gly Asn Ala Asn Tyr Asn Gln Gln Phe Lys
1               5                   10                  15

Gly

<210> SEQ ID NO 7
<211> LENGTH: 13
<212> TYPE: PRT
<213> ORGANISM: Mus musculus
<220> FEATURE:
<223> OTHER INFORMATION: SAP-E CDRH3 amino acid

<400> SEQUENCE: 7

Gly Asp Phe Asp Tyr Asp Gly Gly Tyr Tyr Phe Asp Ser
1               5                   10

<210> SEQ ID NO 8
<211> LENGTH: 11
<212> TYPE: PRT
<213> ORGANISM: Mus musculus
<220> FEATURE:
<223> OTHER INFORMATION: SAP-E CDRL1 amino acid

<400> SEQUENCE: 8

Arg Ala Ser Glu Asn Ile Tyr Ser Tyr Leu Ala
1               5                   10

<210> SEQ ID NO 9
<211> LENGTH: 7
<212> TYPE: PRT
<213> ORGANISM: Mus musculus
<220> FEATURE:
<223> OTHER INFORMATION: SAP-E CDRL2 amino acid

<400> SEQUENCE: 9

Asn Ala Lys Thr Leu Ala Glu
1               5

<210> SEQ ID NO 10
<211> LENGTH: 9
<212> TYPE: PRT
<213> ORGANISM: Mus musculus
<220> FEATURE:
<223> OTHER INFORMATION: SAP-E CDRL3 amino acid

<400> SEQUENCE: 10

Gln His His Tyr Gly Ala Pro Leu Thr
1               5
```